US012716098B2

(12) United States Patent
Chen

(10) Patent No.: US 12,716,098 B2
(45) Date of Patent: Aug. 25, 2026

(54) GENETIC DIAGNOSTIC TOOL FOR FACIOSCAPULOHUMERAL MUSCULAR DYSTROPHY (FSHD)

(71) Applicant: CHILDREN'S NATIONAL MEDICAL CENTER, Washington, DC (US)

(72) Inventor: Yi-Wen Chen, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 721 days.

(21) Appl. No.: 18/000,256

(22) PCT Filed: May 28, 2021

(86) PCT No.: PCT/US2021/035018
§ 371 (c)(1),
(2) Date: Nov. 29, 2022

(87) PCT Pub. No.: WO2021/243303
PCT Pub. Date: Dec. 2, 2021

(65) Prior Publication Data

US 2023/0220473 A1 Jul. 13, 2023

Related U.S. Application Data

(60) Provisional application No. 63/031,999, filed on May 29, 2020.

(51) Int. Cl.
*C12Q 1/6883* (2018.01)
*C12Q 1/6869* (2018.01)
*C12Q 1/6806* (2018.01)

(52) U.S. Cl.
CPC ......... *C12Q 1/6883* (2013.01); *C12Q 1/6806* (2013.01); *C12Q 1/6869* (2013.01); *C12Q 2600/154* (2013.01); *C12Q 2600/156* (2013.01)

(58) Field of Classification Search
CPC ................ C12Q 1/6883; C12Q 1/6869; C12Q 2600/154; C12Q 1/6827; C12Q 2600/156
See application file for complete search history.

(56) References Cited

U.S. PATENT DOCUMENTS

| | | | |
|---|---|---|---|
| 2004/0126759 A1 | 7/2004 | Baughn et al. | |
| 2006/0115829 A1 | 6/2006 | Mao et al. | |
| 2007/0161031 A1 | 7/2007 | Trinklein et al. | |
| 2013/0130924 A1 | 5/2013 | Walrafen et al. | |
| 2013/0288976 A1* | 10/2013 | van der Maarel ... | C12Q 1/6883 514/17.7 |
| 2017/0260590 A1 | 9/2017 | Eltoukhy et al. | |
| 2017/0306403 A1 | 10/2017 | Jones et al. | |
| 2018/0147256 A1 | 5/2018 | Van Der Maarel et al. | |
| 2019/0080045 A1 | 3/2019 | Wei et al. | |
| 2019/0153528 A1 | 5/2019 | Brown | |
| 2020/0048688 A1 | 2/2020 | Xiao et al. | |

FOREIGN PATENT DOCUMENTS

WO WO 2015/143062 A1 9/2015

OTHER PUBLICATIONS

Watson (Laboratory Investigation, 2020, 100:135-146, published online Jul. 4, 2019).*
Zampatti (neurogenetics, 2019, 20:57-64).*
Jones et al. (Clinical Epigenetics, 2014, 6:23, pp. 1-16).*
International Search Report & Written Opinion issued Oct. 19, 2021 in PCT/US2021/035018 filed on May 28, 2021, citing documents 1-11, 15 & 24 therein, 16 pages.
Hamanaka et al., "Homozygous nonsense variant in *LRIF1* associated with facioscapulohumeral muscular dystrophy", Neurology, vol. 94, No. 23, Jun. 9, 2020, 7 pages.
Extended European Search Report issued Jun. 18, 2024 in European Patent Application No. 21814592.8, 11 pages.

* cited by examiner

*Primary Examiner* — Sarae L Bausch
(74) *Attorney, Agent, or Firm* — Oblon, McClelland, Maier & Neustadt, L.L.P.

(57) ABSTRACT

Disclosed are compositions and methods for the diagnosis of Facioscapulohumeral muscular dystrophy (FSHD) using nanopore sequencing and CRISPR/Cas9 enrichment of D4Z4 containing sequences to determine the number of repeats in a D4Z repeat region and methylation of the nucleotide bases in this region.

22 Claims, 12 Drawing Sheets

Specification includes a Sequence Listing.

Figure 2A:
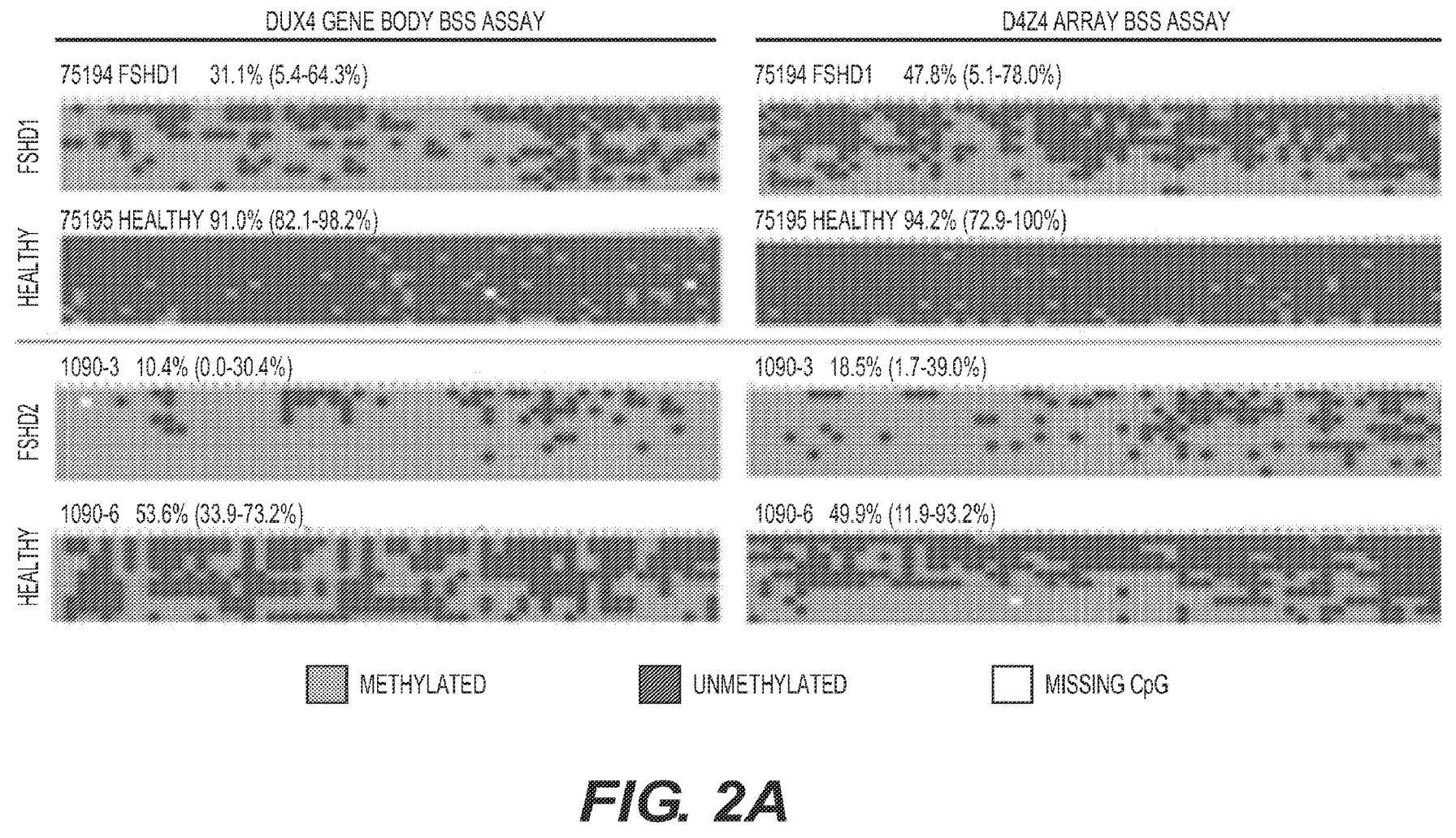

DUX4 GENE BODY BSS ASSAY

D4Z4 ARRAY BSS ASSAY

FSHD1

75194 FSHD1 31.1% (5.4-64.3%)

75194 FSHD1 47.8% (5.1-78.0%)

HEALTHY

75195 HEALTHY 91.0% (82.1-98.2%)

75195 HEALTHY 94.2% (72.9-100%)

FSHD2

1090-3 10.4% (0.0-30.4%)

1090-3 18.5% (1.7-39.0%)

HEALTHY 1090-6 53.6% (33.9-73.2%)

1090-6 49.9% (11.9-93.2%)

METHYLATED

UNMETHYLATED

MISSING CpG

SEQUENCE LISTING

```
<160> NUMBER OF SEQ ID NOS: 16

<210> SEQ ID NO 1
<211> LENGTH: 20
<212> TYPE: RNA
<213> ORGANISM: Artificial Sequence
<220> FEATURE:
<223> OTHER INFORMATION: gRNA for D4Z4 region

<400> SEQUENCE: 1

ccuauuaaac gucacggaca                                                   20


<210> SEQ ID NO 2
<211> LENGTH: 20
<212> TYPE: RNA
<213> ORGANISM: Artificial Sequence
<220> FEATURE:
<223> OTHER INFORMATION: gRNA for D4Z4 region

<400> SEQUENCE: 2
```

gauaccgaca gcaauagucc 20

<210> SEQ ID NO 3
<211> LENGTH: 20
<212> TYPE: RNA
<213> ORGANISM: Artificial Sequence
<220> FEATURE:
<223> OTHER INFORMATION: gRNA for D4Z4 region

<400> SEQUENCE: 3
aaaucuucua uaggauccac 20

<210> SEQ ID NO 4
<211> LENGTH: 20
<212> TYPE: RNA
<213> ORGANISM: Artificial Sequence
<220> FEATURE:
<223> OTHER INFORMATION: gRNA for D4Z4 region

<400> SEQUENCE: 4
uacuucugua cugaucaccc 20

<210> SEQ ID NO 5
<211> LENGTH: 20
<212> TYPE: RNA
<213> ORGANISM: Artificial Sequence
<220> FEATURE:
<223> OTHER INFORMATION: gRNA for SCHMD1 gene

<400> SEQUENCE: 5
gacauucgca ugaauuugaa 20

<210> SEQ ID NO 6
<211> LENGTH: 20
<212> TYPE: RNA
<213> ORGANISM: Artificial Sequence
<220> FEATURE:
<223> OTHER INFORMATION: gRNA for SCHMD1 gene

<400> SEQUENCE: 6
aauacugcag uacacuucuc 20

<210> SEQ ID NO 7
<211> LENGTH: 20
<212> TYPE: RNA
<213> ORGANISM: Artificial Sequence
<220> FEATURE:
<223> OTHER INFORMATION: gRNA for SCHMD1 gene

<400> SEQUENCE: 7
uaguucaccu cccucugguu 20

<210> SEQ ID NO 8
<211> LENGTH: 20
<212> TYPE: RNA
<213> ORGANISM: Artificial Sequence
<220> FEATURE:
<223> OTHER INFORMATION: gRNA for SCHMD1 gene

<400> SEQUENCE: 8
cuaacuccag aauugccaca 20

<210> SEQ ID NO 9
<211> LENGTH: 20
<212> TYPE: RNA

<213> ORGANISM: Artificial Sequence
<220> FEATURE:
<223> OTHER INFORMATION: gRNA for DNMT3B gene

<400> SEQUENCE: 9
uucuuccugc accaauggac 20

<210> SEQ ID NO 10
<211> LENGTH: 20
<212> TYPE: RNA
<213> ORGANISM: Artificial Sequence
<220> FEATURE:
<223> OTHER INFORMATION: gRNA for DNMT3B gene

<400> SEQUENCE: 10
uuccaacaac aauaugcccc 20

<210> SEQ ID NO 11
<211> LENGTH: 20
<212> TYPE: RNA
<213> ORGANISM: Artificial Sequence
<220> FEATURE:
<223> OTHER INFORMATION: gRNA for DNMT3B gene

<400> SEQUENCE: 11
caccauggca accugcacgu 20

<210> SEQ ID NO 12
<211> LENGTH: 20
<212> TYPE: RNA
<213> ORGANISM: Artificial Sequence
<220> FEATURE:
<223> OTHER INFORMATION: gRNA for DNMT3B gene

<400> SEQUENCE: 12
uggggucuca auacccgggg 20

<210> SEQ ID NO 13
<211> LENGTH: 20
<212> TYPE: RNA
<213> ORGANISM: Artificial Sequence
<220> FEATURE:
<223> OTHER INFORMATION: gRNA for LRIF1 gene

<400> SEQUENCE: 13
gacaguaugu uuauguggug 20

<210> SEQ ID NO 14
<211> LENGTH: 20
<212> TYPE: RNA
<213> ORGANISM: Artificial Sequence
<220> FEATURE:
<223> OTHER INFORMATION: gRNA for LRIF1 gene

<400> SEQUENCE: 14
uagugcuugc cuauggcaua 20

<210> SEQ ID NO 15
<211> LENGTH: 20
<212> TYPE: RNA
<213> ORGANISM: Artificial Sequence
<220> FEATURE:
<223> OTHER INFORMATION: gRNA for LRIF1 gene

<400> SEQUENCE: 15
uuggauugca ucauaagggu 20

-continued

```
<210> SEQ ID NO 16
<211> LENGTH: 20
<212> TYPE: RNA
<213> ORGANISM: Artificial Sequence
<220> FEATURE:
<223> OTHER INFORMATION: gRNA for LRIF1 gene

<400> SEQUENCE: 16

uuagccagac aaccuggauu                                                20
```

GENETIC DIAGNOSTIC TOOL FOR FACIOSCAPULOHUMERAL MUSCULAR DYSTROPHY (FSHD)

CROSS-REFERENCE TO A RELATED APPLICATION

This application claims priority to U.S. Provisional Application No. 63/031,999, filed May 29, 2020, which is hereby incorporated by reference for all purposes.

REFERENCE TO A SEQUENCE LISTING

The present specification makes reference to a Sequence Listing submitted electronically as a .txt file named "537147WO_ST25.txt". The .txt file was generated on May 21, 2021 and is 4,096 bytes in size. The entire contents of the Sequence Listing are hereby incorporated by reference. The Sequence Listing is an integral part of this disclosure/description.

BACKGROUND OF THE INVENTION

Field of the Invention

This disclosure pertains to the fields of medicine and medical genetics especially with respect to the diagnosis of Facioscapulohumeral muscular dystrophy (FSHD).

Description of the Related Art

Facioscapulohumeral muscular dystrophy (FSHD) is one of the most common muscular dystrophies, affecting approximately 39,500 individuals in US and 924,000 individuals worldwide.

FSHD1 is an autosomal dominant form of muscular dystrophy which means that an affected parent has a 50 percent chance of passing the genetic defect on to each child. Approximately 95 percent of FSHD cases are known as Type 1 (chromosome 4-linked FSHD; also called FSHD1 or Type 1A).

FSHD1 is caused by aberrant expression of double homeobox 4 (DUX4) due to epigenetic changes of the D4Z4 macrosatellite repeat region at chromosome 4q35. The aberrant expression of DUX4 causes misregulation of numerous downstream genes and pathways, which in turn lead to muscle pathologies.

Analysis of the D4Z4 array at chromosome 4q35 presents a number of challenges including the length of each repeat unit being about 3.3 kb, a large number of repeats in each array, presence of a highly similar repeat array on chromosome 10 and DNA methylation in each array/repeat. Moreover, several sequential diagnostic assays are needed to distinguish D4Z4 arrays or repeats on chromosome 4 from those of chromosome 10, and to determine involvement of FSHD1 and FSHD2.

Current genetic testing for FSHD1 is directed to detecting a contracted D4Z4 array using pulsed-field gel electrophoresis (PFGE) in combination with Southern blotting. These prior methods are time consuming, labor intensive, not precise, and very expensive. In addition these methods do not assess epigenetic changes associated with FSHD.

FSHD is caused by mutations that actually increase the expression of DUX4, FSHD type 2 is clinically indistinguishable from FSHD1, but without the contraction of the D4Z4 domain on chromosome 4 to 1-10 repeat units. People with FSHD2 (5% of cases) have 11 or more D4Z4 units like people without FSHD.

There is no effective treatment for FSHD and current methods and tools for FSHD genetic diagnoses are costly and labor intensive.

In view of these problems with and drawbacks to current technologies, the inventors should develop tools and methods that can more effectively, accurately and easily diagnose FSHD and reduce labor costs and expense of diagnosis.

BRIEF SUMMARY OF THE INVENTION

The disclosure is directed to methods and compositions for diagnosing facioscapulohumeral muscular dystrophy (FSHD) and to methods and compositions for detecting either type 1 FSHD ("FSHD1") or type 2 FSHD ("FSHD2").

One aspect of this technology is a method for diagnosing FSHD1 by determining the number of repeats in a D4Z4 array of a subject where a number of repeats that is 10 or less indicates presence of FSHD1 or a risk of developing FSHD1 as determined by nanopore long-read sequencing. Advantageously the method disclosed herein obtains long reads that cover the entire D4Z4 region which allow it to accurately and easily determine the number of D4Z4 repeats in comparison to existing methods such as Southern blotting. Methods involving next generation sequencing are hampered by the long length, about 3.3 kb, of each repeat unit in a D4Z4 array. Nanopore long-read sequencing can obtain the whole D4Z4 array, however the coverage is limiting using current platform, thus an enrichment method is used in combination with the Nanopore long-read sequencing assay. To obtain this more effective method, the inventors developed a CRISPR/Cas9 long-lead protocol which enriches for the D4Z4 region which uses guide RNAs (gRNAs) which flank the D4Z4 array between the p13e11 region and the pLAM region. This protocol enriches for DNA which encompasses the whole D4Z4 array and thus providing accurate determination of the number of repeats in the sequenced array.

Another aspect of this technology is the determination of the methylation status of DNA in a D4Z4 array where hypomethylation of a contracted array (i.e., having 10 or fewer D4Z4 repeats) in comparison to methylation of the D4Z4 array in a normal subject not having FSHD is further indicative of FSHD1 in the subject with a contracted array (i.e. 10 or fewer D4Z4 repeats), or indicative of FSHD2 in a subject who may have a non-contracted array (i.e., 11 or more D4Z4 repeats). This test in combination with determination of a contracted D4Z4 array provides an accurate and convenient test for FSHD1 which determines both genetic (contracted D4Z4 array) and epigenetic changes (e.g., DNA hypomethylation) associated with, or determinative of, FSHD1.

Moreover, using the method, the polyadenylation signal in the pLAM region is sequenced and examined, thus one can determine whether an intact polyadenylation signal is present in the allele.

Another aspect of this technology is a method for diagnosing FSHD2 using CRISPR/Cas9 long-read enrichment protocol similar to that described for D4Z4 above, which enriches the SMCHD1, DNMT3B, or LRIF1 regions. These regions are sequenced to identify mutations in epigenetic regulatory proteins that establish repression at the D4Z4 arrays, for example, mutations that result in hypomethylation of the D4Z4 array and aberrant transcription of DUX4. Functional poly-adenylation of DUX4 transcripts in FSHD1 and FSHD2 leads to expression of DUX4 protein and subsequent disease. In normal subjects DUX4 expression is suppressed.

Other aspects of this technology pertain to compositions and kits for detection or diagnosis of FSHD1 or FSHD2, such as compositions or kits containing the gRNAs described by SEQ ID NOS: 1-16 which are used for CRISPR/Cas9 long-lead enrichment.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 2A shows FSHD bisulfite sequencing ("BSS") assays. FSHD1 has DNA hypomethylation only on the contracted allele (gene body assay: dark gray/orange and light gray/blue bars are assayed).

FIG. 3A shows an 82 kb read which contains 8 D4Z4 repeats and the flanking region.

FIG. 3B shows the unaffected allele that was captured in the 102 kb read which contains 32 repeats. The D4Z4 repeats are indicated by dashes at the bottom of each figure.

DETAILED DESCRIPTION

Facioscapulohumeral muscular dystrophy (FSHD) is caused by aberrant expression of double homeobox protein 4 (DUX4) due to epigenetic changes of the D4Z4 repeat array at chromosome 4q35. The epigenetic changes are caused by (i) contraction of the D4Z4 array from 11-150 repeat units in unaffected individuals to 1-10 repeat units in roughly 95% of patients (FSHD1) or (ii) mutations in several epigenetic regulators of the region (FSHD2). However, due to the large size of each repeat unit in a D4Z4 array (3.3 kb), it is challenging to determine the repeat number using PCR or next generation sequencing approaches.

Figure 1:
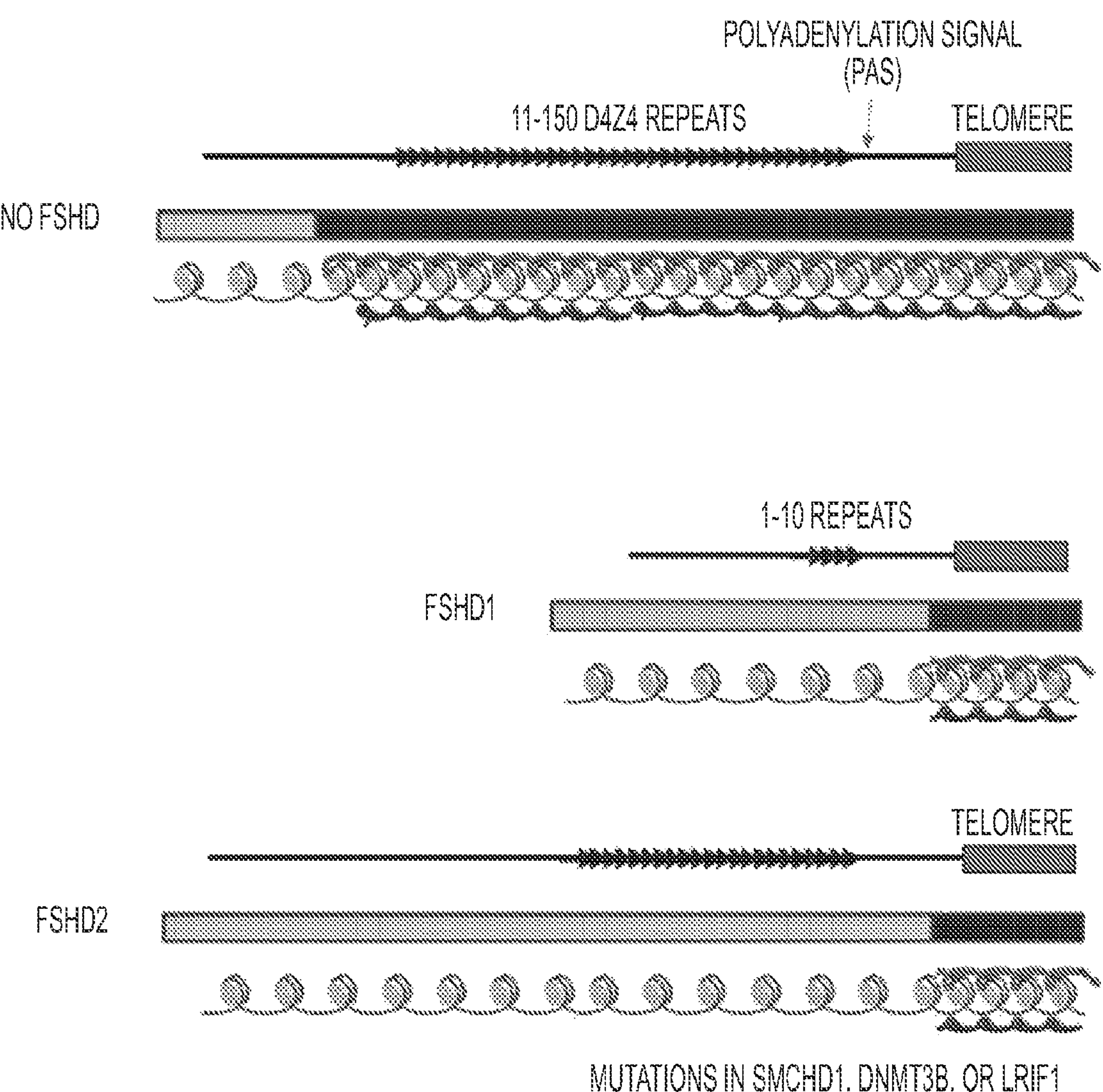
FIG. 1 shows the genetic mechanisms of FSHD. Two genomic features are required to cause FSHD. The first is a loosening of chromatin structure of the D4Z4 region which allows transcription of DUX4. This is caused by a contraction of the D4Z4 array from 11-150 repeats to 1-10 repeats in patients with FSHD1; and mutations in SMCHD1, DNMT3B or LRIF1 in patients with FSHD2. The second genomic feature is a functional polyadenylation signal downstream of the last D4Z4 repeat, which allows the DUX4 transcript to be stabilized for protein translation.

The disease mechanism of FSHD is outlined in FIG. 1. Two genomic features are thought to be required to cause FSHD. The first is a contraction of the D4Z4 array or mutations in SMCHD1, DNMT3B or LRIF1, which loosen chromatin structure of the D4Z4 region, cause DNA hypomethylation of the region and allow transcription of DUX4. The second feature is a functional polyadenylation signal downstream of the last D4Z4 repeat, which allows the DUX4 transcript to be stabilized for protein translation. The DNA methylation status of the D4Z4 region has been shown to distinguish FSHD1 from nonmanifesting and healthy individuals as well as from FSHD2.

As explained below, a novel strategy for FSHD diagnosis was developed using Nanopore long-read sequencing. The assay determines the copy number of D4Z4 and the methylation status of the D4Z4 array region, which provides a fast, cheap and versatile solution for molecular diagnosis of FSHD.

First, the D4Z4 region and other genes that were known to cause or contribute to FSHD2 were enriched for long read-sequencing using Nanopore device. A CRISPR/Cas9-based enrichment protocol is developed to specifically select the D4Z4 arrays, SMCHD1, DNMT3B and, optionally, LRIF1 for nanopore long-read sequencing.

Sixteen gRNAs that specifically target the regions of interest for sequencing were designed SEQ ID NOS, 1-4 are specific for D4Z4; SEQ ID NOs: 5-8 are specific for SMCHD1, SEQ ID NOS: 9-12 are specific for DNMT3B, and SEQ ID NOS: 13-16 are specific for LRIF1.

Second, for the D4Z4 regions, the sequence was analyzed to determine the numbers of D4Z4 repeats in each of the arrays on chromosome 4 and 10 with a focus on the shortened allele. In addition, it can be determined which alleles (A or B allele) were associated with the shortened alleles.

Third, in addition to the D4Z4 array size, DNA methylation in the sequences can be determined, which can be used to confirm the disease status and identify FSHD2 based on the DNA methylation pattern.

Lastly, for the SMCHD1, DNMT3B or LRIF1 genes, the sequences can be analyzed for mutations which contribute to DUX4 expression.

As a result, the assay disclosed herein provides sequence and molecular information for diagnosing both FSHD1 and FSHD2.

As disclosed herein, a CRISPR/Cas9-based enrichment protocol in combination with the Nanopore long-read sequencing was used to specifically target the D4Z4 region. Two guide RNAs flanking the D4Z4 array between the p13e11 region and the pLAM region were used for the enrichment protocol. The inventors successfully obtained complete D4Z4 arrays spanning from the p13e11 region to the pLAM region. In addition, they obtained DNA methylation information of this region and demonstrated hypomethylation in the contracted alleles. Based on these discoveries, the inventors sought to develop a single test that can assess both genetic and epigenetic causes of FSHD to facilitate the molecular diagnosis of FSHD type 1 and type 2.

Embodiments of this disclosure, include but are not limited to the following.

One aspect of this technology is directed to a method of diagnosing Facioscapulohumeral muscular dystrophy (FSHD) in a subject comprising:

screening for FSHD1 by (a1) performing nanopore long-read sequencing on a nucleic acid sample from the subject which has been enriched for DNA sequences comprising a D4Z4 repeat array using CRISPR/Cas 9 and guide RNAs ("gRNAs") which recognize DNA sequences flanking the D4Z4 repeat array;

(b1) measuring the number of D4Z4 repeats in the D4Z4 repeat array and/or measuring the methylation of bases in the D4Z4 repeat array of the sequenced DNA or measuring the methylation of the permissive allele(s) (such as specific D4Z4 4q or 10q alleles that contains functional polyadenylation) of the subject; and (c1) identifying or selecting a subject as having FSHD1 when ten or fewer D4Z4 repeats are detected in the D4Z4 repeat array; or when ten or fewer D4Z4 repeats are detected and when the D4Z4 array of the subject or permissive alleles (such as specific D4Z4 4q or 10q alleles that contain functional polyadenylation) are hypomethylated compared to that in a normal control subject not having FSHD1 and, optionally, (d1) treating FSHD1, FSHD1 symptoms, or providing genetic counseling to the subject when FSHD1 is detected; and/or screening for FSHD2 by:

(a2) performing nanopore long-read sequencing on a nucleic acid sample from the subject which has been enriched for DNA sequences SMCHD1, DNMT3B, or LRIF1 genes using CRISPR/Cas 9 and guide RNAs ("gRNAs") which recognize DNA sequences flanking the SMCHD1, DNMT3B, or LRIF1 genes;

(b2) detecting one or more mutations in the SMCHD1, DNMT3B, or LRIF1 genes which loosen chromatin structure of the D4Z4 region and allow transcription of DUX4, and/or measuring the methylation of bases in the permissive allele and other D4Z4 arrays of the subject; and (c2) identifying or selecting a subject as having FSHD2 when) the D4Z4 repeat array or D4Z4 4q and 10q alleles of the subject are hypomethylated compared to those in a normal control subject not having FSHD2 and when mutations to the SMCHD1, DNMT3B, or LRIF1 regions which loosen chromatin structure of the D4Z4 region and allow transcription of DUX4, are detected; and, optionally, (d2) treating the subject of FSHD2, FSHD2 symptoms, or providing genetic counseling to the subject when FSHD2 is detected.

The nucleic acid sample is preferably obtained from a convenient, non-invasive source and may include tissue samples or liquid biological samples from a subject to be evaluated for FSHD or risk of FSHD. It may be obtained from whole blood, PBMCs, plasma or serum, from buccal tissue, such as by buccal swab, or from saliva, urine or other fluids. It may also be obtained from bone marrow, phlegm, gastric juices, tissue lavage, cultured cells, biopsies (including, but not limited to tissue resection, biopsy phlebotomy, core biopsy), or other tissue preparations.

Preferably, from the standpoint of determining methylation, the nucleic acid is not amplified or processed in a way that would alter its natural epigenetic features, including methylation. Typically, the nucleic acid is isolated, purified or prepared in a form suitable for CRISPR/Cas9 enrichment.

Enrichment may comprise enriching the D4Z4 repeats on chromosome 4 by dephosphorylating the 5' ends of the nucleic acid, adding Cas9 ribonucleoprotein particles and guide RNA (gRNA) specific for D4Z4, and culling the dephosphorylated 5' ends using CRISPR/Cas9, and ligating sequencing adapters to the nucleic acid prior to the nanopore long-read sequencing. Commercially available kits may be used in conjunction with designed guide RNAs ("gRNAs") to enrich target DNA such as that containing D4Z4 repeat arrays or other regions of DNA or genes encoding proteins that affect methylation or that aggravate FSHD. Such kits, their components, reagents and protocols are known and incorporated by reference to hypertext transfer protocol secure://nanoporetech.com/sites/default/files/s3/posters/pdf/cas9-target-enrichment-method-poster-023-v1.0-mar2019. pdf (last accessed May 26, 2021).

In one embodiment, the nucleic acid sample is enriched for DNA comprising, consisting essentially of, or consisting of the D4Z4 repeat array. In a preferred embodiment the CRISPR/Cas9 enrichment uses gRNAs comprising sequences from the P123811 region, 4qA (PLAM), or 4qB regions, which regions flank the D4Z4 repeat array. A region comprising P123811, D4Z4 and 4qA/4qB may be considered a complete array. In alternative embodiments, a partial or incomplete D4Z4 array may be compared to a normal D4Z4 array. A partial array with more than 10 repeats would indicate a low or absent risk of FSHD1.

In one embodiment of this method step (b) comprises measuring the number of D4Z4 repeats in the D4Z4 repeat array and determining the methylation of bases in the D4Z4 repeat array of the sequenced DNA. Preferably both D4Z4 repeat array length analysis and methylation status of the array are performed. Thus, covering situations where length analysis alone may not sufficiently diagnose FSHD or serve as an exclusion criterion.

Comparison of methylation may be performed by comparing the absolute number of methylated bases in two arrays to be compared (e.g., an array from a patient and a normal array), by the average number of methylated bases in two D4Z4 arrays, or by comparing the number or average number of methylated bases in one or more D4Z4 repeats in an array, for example, comparing methylation of the first or last D4Z4 repeat in an array or that of intermediate repeats, such as repeats 2, 3, 4, 5, 6, 7, 8, or 9, or combinations thereof, such as 1 and 2, 1 to 3, 1-4, 1-5, 1 and the last repeat, the last two repeats, 9 and 10, etc.

In another embodiment of this method, useful for identifying a subject having FSHD2, step (b) comprises identifying hypomethylation of bases in the D4Z4 repeat array of the sequenced DNA compared to methylation of bases in DNA from a normal control subject who does not have FSHD, and identifying mutations to the SMCHD1, DNMT3B, or LRIF1 regions which loosen chromatin structure the D4Z4 region and allow transcription of DUX4 compared to SMCHD1, DNMT3B, or LRIF1 regions in a subject not having FSHD. The methylation profile may be based on absolute numbers of methylated bases or on an average number of methylated bases for each compared array as described above.

These genes (including splice variants) are identified by the following accession numbers: SMCHD1 (NM_015295.3), DNMT3B (NM_006892.4, NM_175848.2, NM_175849.2, NM_175850.3, NM_001207055.2), or LRIF1 (NM_018372.4, NM_018372.4. In some embodiments, other variants of these genes may be used in conjunction with the methods and compositions disclosed herein such as variants having at least 99, 99, 99.5, 99.9 or <100% sequence identity with, or which have 1, 2, 5, 10, 20, 30, 40, 50 or more deletions, substitutions, or insertions to genes identified by the sequences described by these accession numbers.

Mutations in SMCHD1 (structural maintenance of chromosomes flexible hinge domain containing 1), DNMT3B (DNA Methyltransferase 3B) [2] and ligand-dependent nuclear receptor-interacting factor 1 (LRIF1) [3] were shown associated with FSHD2; respectively see Lemmers, R. J., et al. (2012) *Digenic inheritance of an SMCHD1 mutation and an FSHD-permissive D4Z4 allele causes facioscapulohumeral muscular dystrophy type 2*, Nat Genet. 2012, 44, 1370-4; van den Boogaard, M. L., et al. (2016) *Mutations in DNMT3B Modify Epigenetic Repression of the D4Z4 Repeat and the Penetrance of Facioscapulohumeral Dystrophy*, American journal of human genetics. 2016, 98, 1020-9; and Hamanaka, K., et al., *Homozygous nonsense variant in LRIF1 associated with facioscapulohumeral muscular dystrophy*, Neurology, 2020, 94, e2441-e2447 (each incorporated by reference).

The design of the methods and tools described herein will allow evaluation of all mutations that are currently known to cause FSHD (1 and 2) using one assay.

In one embodiment, the nucleic acid sample has been enriched for DNA comprising the D4Z4 repeat array using gRNAs selected from the group consisting of those comprising, the sequences described by SEQ ID NOS: 1, 2, 3, or 4. This embodiment may be used to evaluate samples for either presence or risk of FSHD1 or FSHD2. FSHD1 typically manifests a shorter D4Z4 array than a normal control array. FSHD2 sometimes manifests a shorter D4Z4 array than controls.

In another embodiment, the nucleic acid sample has been enriched for DNA comprising the SMCHD1 region, for example, using gRNAs selected from the group consisting of those comprising the sequences described by SEQ ID NOS: 5, 6, 7, or 8.

In another embodiment, the nucleic acid sample has been enriched for DNA comprising the DNMT3B region, for example, using gRNAs selected from the group consisting of those comprising the sequences described by SEQ ID NOS: 9, 10, 11 or 12.

In another embodiment, the nucleic acid sample has been enriched for DNA comprising the LRIF1 region, for example, using gRNAs selected from the group consisting of those comprising the sequences described by SEQ ID NOS: 13, 14, 15, or 16.

In some embodiments of the method disclosed herein, the presence or absence of a functional polyadenylation signal downstream of the last D4Z4 can be determined by nanopore sequencing, by determination of a genetic allele, or by other methods known in the art. The presence of a functional polyadenylation signal sequence can stabilize DUX4 transcripts when the 4qA allele is present and result in aberrant expression of DUX4 protein which can induce FSHD.

In a preferred embodiment of this method nanosequencing base-calling of methylated bases is employed to establish a methylation profile of a test or control enriched DNA. Alternatively, methylation can be determined by sodium bisulfite conversion, different enzymatic cleavage of DNA, or affinity capture of methylated DNA.

The methods disclosed herein may also encompass counseling or treating a subject determined to have FSHD or a risk of developing FSHD. Treatment typically involves symptomatic or supportive treatment or management of FSHD, however it also encompasses pharmacological or biological treatment of the mechanisms producing disease. Thus, the method may comprise treating the subject for at least one FSHD symptom when FSHD or a risk thereof is identified.

Treatment may also encompass providing genetic counseling to the subject or close relatives when FSHD is identified. It may also constitute informing the subject of a negative or differential diagnosis excluding FSHD when FSHD is not identified in the subject.

Another aspect of this disclosure is directed to composition comprising at least one of the gRNAs of SEQ ID NOS: 1-16 and a buffer suitable for action of CRISPR/Cas9. Preferably gRNA sequences flanking each end of a target array are incorporated into a composition. In some embodiments mixtures of four or more gRNAs may be used in multiplex to enrich for two or more target arrays or sequences.

Another aspect of the disclosure is a kit for diagnosing FSHD comprising at least one of the gRNAs of SEQ ID NOS: 1-16, and, optionally, a buffer suitable for action of CRISPR/Cas9, positive or negative control DNA, and/or other equipment or reagents for enriching target DNA using CRISPR/Cas9 enrichment, and or a processor or software for receiving, processing, and displaying data describing length of a D4Z4 array or a methylation status of one or more D4Z4 repeats or a D4Z4 array. A kit may contain swab(s), such as a buccal swab, blood drawing syringes or vacutubes, sample containers optionally containing preservatives for DNA, packaging materials, return mail or courier envelopes or reaction containers. A kit may also contain instructions for use. Any medium capable of storing instructions and communicating them to an end user may be used including package inserts, such as written instructions, or electronic storage media (e.g., magnetic discs, tapes, cartridges), optical media (e.g., CD ROM), and the like. The instructions for use of the kit may also include an address of an internet site which provides instructions.

In one embodiment, the kit described above comprises gRNA consisting of, consisting essentially of or comprising SEQ ID NO: 1, SEQ ID NO: 2, SEQ ID NO: 3, or SEQ ID NO: 4 for enrichment of DNA comprising a D4Z4 array.

In another embodiment, the kit described above comprises gRNA consisting of, consisting essentially of or comprising SEQ ID NO: 5, SEQ NO: 6, SEQ ID NO: 7, or SEQ ID NO: 8 for enrichment of DNA comprising a SMCHD1 region.

In another embodiment, the kit described above comprises gRNA consisting of, consisting essentially of or comprising SEQ ID NO: 9, SEQ ID NO: 10, SEQ ID NO: 11, or SEQ ID NO: 12 for enrichment of DNA comprising a DNMT3B region.

In another embodiment, the kit described above comprises gRNA consisting of, consisting essentially of or comprising SEQ ID NO: 13, SEQ ID NO: 14, SEQ ID NO: 15, or SEQ ID NO: 16 for enrichment of DNA comprising a LRIF1 region.

Facioscapulohumeral muscular dystrophy ("FSHD") is a disorder characterized by muscle weakness and wasting (atrophy). The disorder gets its name from muscles that are affected in the face (facio), around the shoulder blades (scapulo), and in the upper arms (humeral). Hamstring and trunk muscles are affected early on but are less well recognized. Other arm and leg muscles are frequently eventually affected in the course of the disease Symptoms usually appear before age 20, but can begin in infancy or later in adulthood. Severity of the condition varies widely and some people with the disease allele remain asymptomatic. FSHD is most typically characterized by relatively slow disease progression. Specific symptoms and findings may also vary in range and severity, including among affected members of the same family. Life expectancy is not shortened. FSHD is usually inherited as an autosomal dominant genetic condition, but may occur as a sporadic, non-inherited condition. FSHD frequency is Two types of FSHD have been described. FSHD1 (95% of those affected) and FSHD2 (5% of those affected). FSHD1 and FSHD2 have the same signs and symptoms but different genetic causes.

FSHD1 is caused by abnormal expression of the DUX4 gene, which is located in the D4Z4 region of chromosome 4. Normally, the DNA in the D4Z4 region is hypermethylated (has many methyl groups: 1 carbon atom and 3 hydrogen atoms) and includes 11-100 repeated segments of DNA. In individuals with FSHD1, this region of chromosome 4 is shortened and contains 1-10 repeats and fewer methyl groups. The lack of methyl groups allows the DUX4 gene to be "turned on" and produce DUX4 protein in cells and tissues where it is usually not produced, resulting in progressive muscle weakness and atrophy. Generally, a smaller or decreasing number of repeats is associated more severe disease. FSHD1 is an autosomal dominant genetic condition. Dominant genetic disorders occur when only a single copy of an abnormal gene is necessary to cause a particular disease. The abnormal gene can be inherited from either parent or can be the result of a new mutation (gene change) in the affected individual. The risk of passing the abnormal gene from affected parent to offspring is 50% for each pregnancy. The risk is the same for males and females. In approximately 30 percent of individuals with FSHD1, there is no apparent family history of the disorder and in these people FSHD is thought to be caused by new mutations. FSHD appears to affect males and females in relatively equal numbers. Its estimated prevalence is between four and ten per 100,000 people.

FSHD2 is an autosomal dominant genetic condition. People with FSHD2 have a mutation in the SMCHD1 gene that results in demethylation of the D4Z4 region, allowing misexpression of the DUX4 gene and resulting in progressive muscle weakness and atrophy.

D4Z4 repeat. A repeat unit of approximately 3.3 kb in length forming part of a D4Z4 array.

D4Z4 array. A grouping of one or more D4Z4 repeating subunits. FSHD1 patients have arrays (10 or fewer repeats) shorter than subjects without FSHD1 (longer than 10 repeats). A complete array may contain P123811, D4Z4 and 4qA/4qB.

Chromosome 4 and chromosome 10 backgrounds. Some Chromosome 4 backgrounds are categorized as permissive for FSHD disease or non-permissive to FSHD when D4Z4 contracts. Chromosome 10 repeats are typically non-permissive. Essentially, D4Z4 contractions to 1-10 units on permissive chromosomes are pathogenic, while contractions on non-permissive chromosomes are non-pathogenic. A permissive allele typically comprises the D4Z4 repeat array and D4Z4 repeats.

Chromosome 4 and 10 are directly identified by sequences that are specific to these chromosomes 4 and 10. Although sequences on the two chromosomes are highly similar, there are polymorphisms which distinguish the two.

The D4Z4 repeat array can be located at chromosome 4 or 10. In general, the shortened (1-10 repeats) D4Z4 array on chromosome 10 does not cause FSHD because the polyadenylation signal downstream of the last repeat is not functional on chromosome 10, even though it is a pLAM sequence. Thus, it usually is not a permissive allele for FSHD. However, in rare situations, the shortened D4Z4 on chromosome 10 can cause disease if the polyadenylation signal is functional and it the DNA of the D4Z4 region is hypomethylated.

FSHD is typically caused by (i) a contracted D4Z4 array of a permissive allele on chromosome 4 which causes hypomethylation of the contracted D4Z4 on chromosome 4 and/or mutations in one of the FSHD2 genes which cause hypomethylation of the D4Z4 on both Chromosomes 4 and 10; these cause de-repression of DUX4 transcription; in combination with (ii) and intact polyadenylation signal which stabilizes DUX4 mRNAs for translation.

While this is critical, the polyadenylation signal is usually not checked in current diagnosis methods because it is hard to check. Instead, a check is made of whether the allele is a 4qA allele which contains the pLAM region, which in turn contains the functional polyadenylation signal. However, this is generally applicable only to a pLAM on Chromosome 4. The 4qB allele does not have the polyadenylation signal so is not permissive.

The method as disclosed herein checks the D4Z4 repeat number, determines sequences on Chromosome 4 or 10, determines the presence of the polyadenylation signal, and mutational status of the FSHD2 related genes providing comprehensive information needed to diagnose FSHD.

4qA and 4qB variants of the 4qter subtelomere. Facioscapulohumeral muscular dystrophy (FSHD) is the third most common inherited muscular dystrophy with markedly clinical variability and complex genetic causes. FSHD is uniquely associated with the 4qA variant. The 4qA and 4qB variant determination may be performed by methods known in the art and used to further characterize presence or risk of FSHD.

Diagnosing includes assessing or quantifying a risk, such as a genetic risk, of a disease, disorder or condition such as FSHD, assessing or quantifying the severity of such a disease, disorder or condition, or identifying or recognizing a subject having a particular disease, disorder or condition such as FSHD1 or FSHD2. It also includes differential diagnosis of a disease and may also include a disease, disorder or condition prognosis or a forecast of a likely course of the disease, disorder or condition in a subject or in a subject's offspring.

Nanopore sequencing is a third generation approach used in the sequencing of biopolymers—specifically, polynucleotides in the form of DNA or RNA. The biological or solid-state membrane, where the nanopore is found, is surrounded by electrolyte solution. The membrane splits the solution into two chambers. A bias voltage is applied across the membrane inducing an electric field that drives charged particles, in this case the ions, into motion. This effect is known as electrophoresis. For high enough concentrations, the electrolyte solution is well distributed and all the voltage drop concentrates near and inside the nanopore. This means charged particles in the solution only feel a force from the electric field when they are near the pore region. This region is often referred as the capture region. Inside the capture region, ions have a directed motion that can be recorded as a steady ionic current by placing electrodes near the membrane. A nano-sized polymer such as DNA or RNA placed in one of the chambers. This molecule also has a net charge that feels a force from the electric field when it is found in the capture region. The molecule approaches this capture region aided by Brownian motion and any attraction it might have to the surface of the membrane. Once inside the nanopore, the molecule translocates through via a combination of electrophoretic, electro-osmotic and sometimes thermo-phoretic forces. Inside the pore the molecule occupies a volume that partially restricts the flow of ions, observed as an ionic current drop.

Based on various factors such as geometry, size and chemical composition (including type of nucleotide and whether a nucleotide is methylated), the change in magnitude of the ionic current and the duration of the translocation will vary. Different molecules can then be sensed and potentially identified based on this modulation in ionic current. Various nanopore sequencing procedures are known and incorporated by reference to hypertext transfer protocol secure://en.wikipedia.org/wiki/Nanopore_sequencing (last accessed May 21, 2021). Using nanopore sequencing, a single molecule of DNA or RNA can be sequenced without the need for PCR amplification or chemical labeling of the sample.

CRISPR/Cas9 enrichment. The D4Z4 region of interest contained within a native DNA sample and epigenetic modifications (such as methylation) is enriched for nanopore sequencing using a PCR-free enrichment method using Cas9. Native strands are sequenced, thus fragment length and epigenetic modifications are preserved. In the method, sample DNA is dephosphorylated to prevent ligation. Cas9 is then used to cleave the DNA at predetermined sites (e.g., at sites flanking the D4Z4 region), exposing ligatable ends. All 3' ends are dA-tailed and sequencing adapters are ligated only to the cleaved ends and the entire library is then added to the flow cell. The fraction of reads corresponding to the ROI is enriched several thousand-fold, enabling many samples to be nu on the same flow cell, or a lower-cost flow cell to be used.

Methylation pattern comparison. Methylation of nucleotides in a D4Z4 array may be based comparison of similar length arrays, for example, comparison of repeats 1-4 from a longer normal array with a shorter, 4 repeat, D4Z4 array from a FSHD patient. Alternatively, the total number of methylated nucleotides in a D4Z4 array may be compared to the total number of methylated nucleotides in another array.

The disclosed method is the only method that can determine number of methylated cytosines in each individual molecule in this region. Based on our preliminary data shown in FIG. 12, the methylation is reduced to approximately 30% in the contracted allele in comparison to the unaffected D4Z4 repeats Based on our data, we preferably d determine methylation of all repeats. In some embodiments, only methylation of the last or latter repeats is measured as methylation of the first or earlier repeats may be low for both affected and unaffected alleles.

Sequence identity. In a preferred embodiment, BLASTN may be used to identify a polynucleotide sequence having at least 80%, 85%, 87.5%, 90%, 92.5%, 95%, 97.5%, 98%, 99%, 99.5, 99.9% or <100% sequence identity to a reference polynucleotide such as a polynucleotide associated with FSHD such as a D4Z4 repeat or array, or a gRNA. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to hypertext transfer protocol secure://blast.ncbi.nlm.nih.gov/Blast.cgi?PROGRAM=blastn&PAGE_TYPE=BlastSearch&LINK_LOC=blasthome (last accessed May 24, 2021). Guide polynucleotides as used herein, such as those of SEQ ID NOS: 1-16, may also be modified by deletion, substitution or insertion of one or more nucleotides from or into a gRNA sequence. For example, among different subjects. minor natural sequence variations may occur among DNA sequences encoding a gRNA contact site in a D4Z4 repeat or array or other genes or DNA regions such as SMCHD1, DNMT3B or LRIF1. The gRNA sequences disclosed herein may be modified by substitution, deletion or insertion of 1, 2, 3, 4, 5 or more nucleotides to compensate for these natural variations.

Guide RNA ("gRNA") is a piece of RNA that functions as a guide for RNA- or DNA-targeting enzymes, with which they form complexes. These enzymes may delete, insert or otherwise alter a targeted RNA or DNA. They may occur naturally, serving important functions, but can also be designed to be used for targeted editing, such as with CRISPR-Cas9. This term refers to guide RNAs including, but not limited to, the gRNAs described by SEQ ID NOS: 1-16 and their equivalents, such as gRNAs having one, two, or three insertions, deletions of substitutions of a nucleotide.

SMCHD1. Structural maintenance of chromosomes flexible hinge domain-containing protein 1 (SMCHD1) has been implicated in X-chromosome inactivation, imprinting, and DNA damage repair, and mutations in SMCHD1 can cause facioscapulohumeral muscular dystrophy. Information about this gene and the protein it encodes as well as its functions and genetic variants are described by and incorporate by reference to hypertext transfer protocol secure://www.ncbi.nlm.nih.gov/gene/23347 (last accessed May 27, 2021). SMCHD1 structural maintenance of chromosomes flexible hinge domain containing 1 [*Homo sapiens* (human)] Gene ID: 23347, updated on 18 May 2021.

DNMT3B. DNA methyltransferase 3 beta. Information about this gene, the protein it encodes, as well as its functions and genetic variants are incorporated by reference to hypertext transfer protocol secure://www.ncbi.nlm.nih.gov/gene/1789 (last accessed May 27, 2021). DNMT3B DNA methyltransferase 3 beta [*Homo sapiens* (human)] Gene ID: 1789, updated on 18 May 2021.

LRIF1—ligand dependent nuclear receptor interacting factor 1. Information about this gene, the protein it encodes, as well as its functions and genetic variants are incorporated by reference to hypertext transfer protocol secure://www.ncbi.nlm.nih.gov/gene/?term=lrif1 (last accessed May 27, 2021). LRIF1 ligand dependent nuclear receptor interacting factor 1 [*Homo sapiens* (human)] Gene ID: 55791, updated on 18 May 2021.

A control is an alternative subject or sample used in an experiment for comparison purposes. A control can be "positive" or "negative." Positive controls measure an expected response and negative controls provide reference points for samples where no response is expected. For example, a positive control DNA for FSHD1 may comprise DNA having a D4Z4 array of 10 or fewer repeats and a negative control from a subject without FSHD1 may have a D4Z4 array that is longer than 10 repeats. Similarly, positive methylation controls may be hypomethylated compared to negative controls from health subjects without FSHD.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "subject" refers to any individual, including patients and control subjects, from whom a DNA sample is obtained for evaluation of the length of D4Z4 array length or for epigenetic characteristics of their DNA, including whether the DNA is normally methylated, hypomethylated, or hyper methylated. The term "patient" refers to a subject under the treatment of a physician or other caregiver.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Treatment of FSHD is usually limited to management of its symptoms. Medical management may include administration of anti-inflammatory drugs, or NSAIDS or other analgesics, to improve comfort and mobility; exercise especially of muscles that are still relatively strong and resting weakened muscles, surgical or mechanical assistance, for example, a surgical procedure to stabilize the shoulder blades; prescription or recommendation of orthoses, such as back supports, corsets, girdles, and special bras to help compensate for weakening of muscles in the upper and lower back, or use of lower leg braces, or ankle-foot orthoeses; or therapeutic massage or application of warm, moist heat. FSHD, especially early onset FSHD, may also be managed by physical, occupational or speech therapies. Dietary therapy may also be considered, such as weight management to reduce load or supplements such as creatine which should be performed under medical supervision. Antiosteoporotic medicines may be administered to patients experiencing hone loss including those described by and incorporated by reference to hypertext transfer protocol secure://www.drugs.com/condition/osteoporosis.html. Pharmaceuticals such as Losmapimod or other drugs or biologics including treatment with gene therapy, small molecules, or stem cells, which reduce the expression of or activity of the DUX4 gene or protein may be administered.

Genetic counseling helps individuals, families and couples affected by or at risk for FSHD to work through the process of genetic testing for the disease. Genetic counseling also helps individuals, families and couples as they plan to have a baby. Prenatal and in vitro fertilization pre-implantation genetic (PGD IVF) tests for FSHD1 or FSHD2 as disclosed herein may be performed. Genetic counselors help couples consider possible scenarios and alternatives, such as having a child with FSHD, adoption or artificial insemination.

Example 1

Methylation Status and Repeats can be Used to Diagnose FSHD

One innovative strength of this disclosure is the unique cohort of early onset FSHD clinical samples complete with detailed clinical evaluations that allows for the investigation of the genetic and epigenetic determinants that distinguish this severe form of FSHD from the typical adult onset FSHD for the first time. Although FSHD1 and FSHD2 are caused by mutations in different genomic regions, all known mutations lead to epigenetic de-repression of the D4Z4 region and allow the pathogenic expression of DUX4.

Figure 2B:
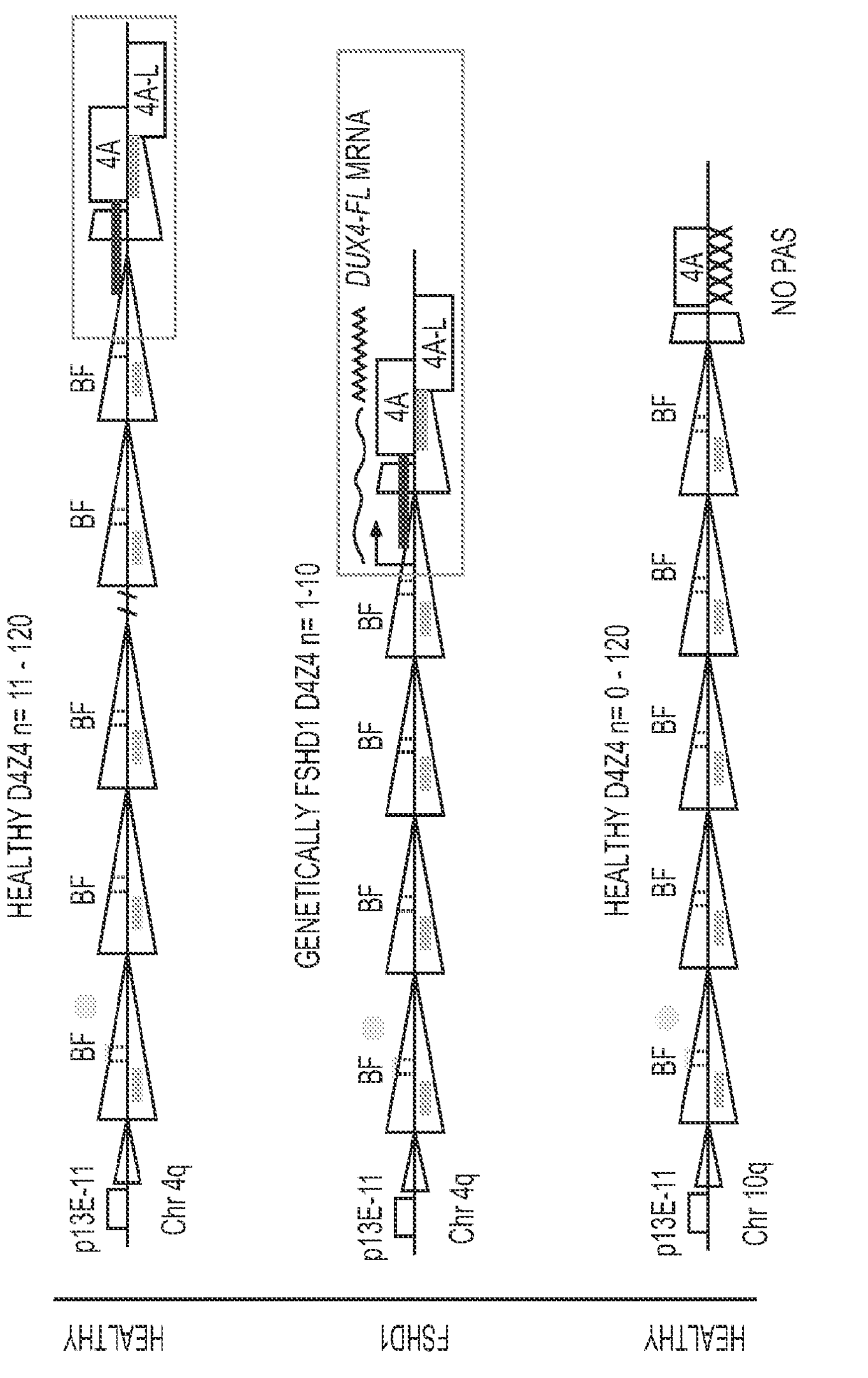
FIG. 2B. FSHD2 is hypomethylated on all D4Z4 repeating units ("RUs") of 4q and 10q alleles (D4Z4 array assay; bars inside triangles are assayed). The pathogenic distal D4Z4 repeat with the DUX4 gene is in the FSHD1 box on the right. Equipment, materials and protocols for characterization of the methylation profiles of DNA are described by and incorporated by reference to Jones, T. I., et al., *Identifying diagnostic DNA methylation profiles for facioscapulohumeral muscular dystrophy in blood and saliva using bisulfite sequencing*. Clinical Epigenetics. 2014, 6, 23, doi: 10.1186/1868-7083-6-73.

As shown in FIG. 2, the DNA hypomethylation pattern is different between FSHD1 and FSHD2. While FSHD1 has DNA hypomethylation only on the contracted allele, the FSHD2 is hypomethylated on all D4Z4 RUs of 4q and 10q alleles.

Figures 3A, 3B:
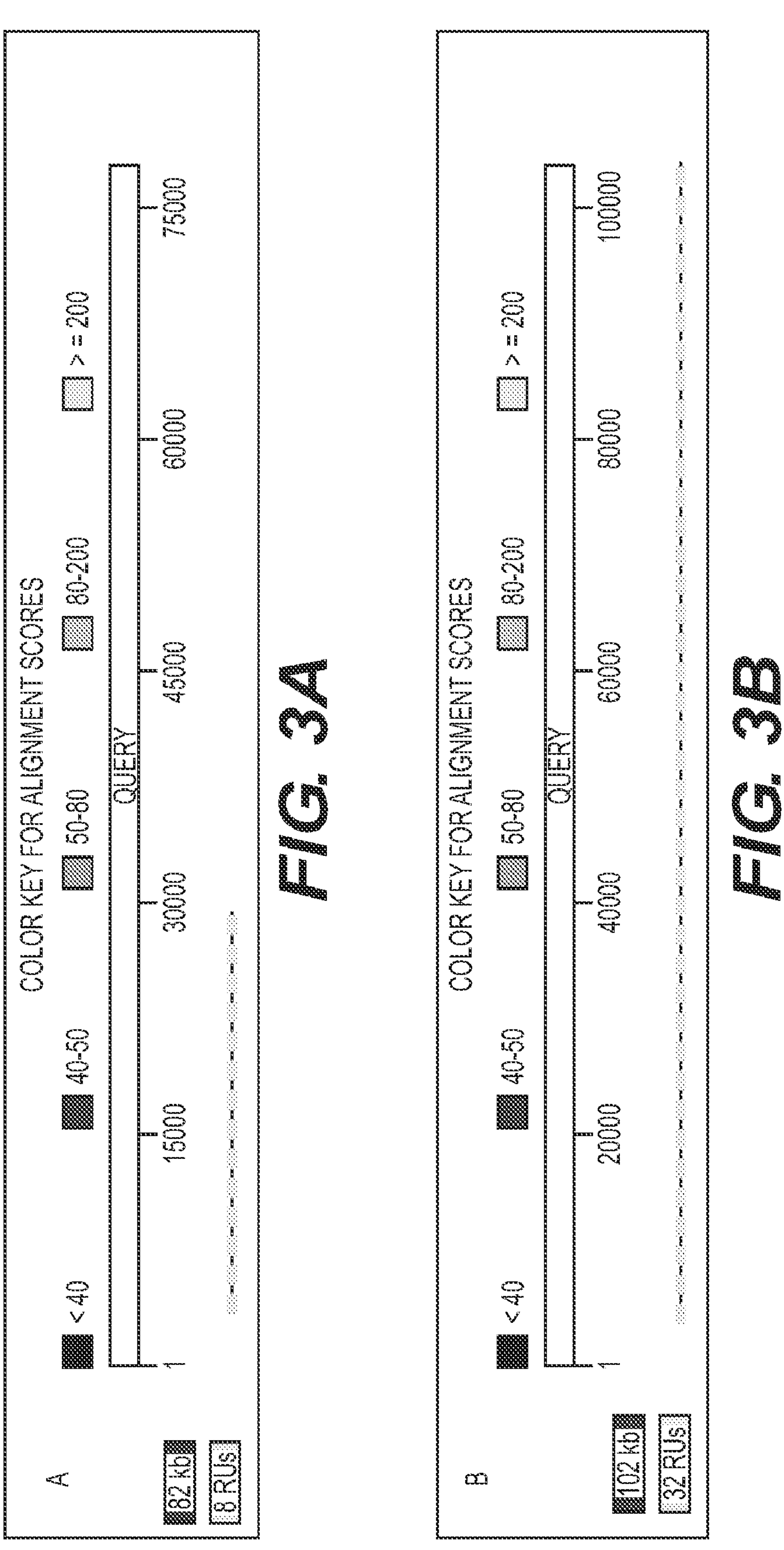
FIGS. 3A and 3B show long-read sequencing assay for FSHD. Two of the long-reads contain the D4Z4 repeats are presented as examples.

A DNA hypomethylation pattern was observed that is not typical for FSHD1 in the early onset FSHD1 cohort. The levels and patterns are distinctly different from FSHD1 and FSHD2 (FIGS. 3A and 3B).

The Nanopore assay can be used which is designed to determine the copy number of D4Z4 and methylation status of the D4Z4 array, which revolutionized the molecular diagnosis of FSHD by providing a fast and accurate diagnostic method. Data was generated to demonstrate feasibility using FSHD DNA.

Despite the great potential of Nanopore sequencing technology, dealing with long-read sequencing data in many aspects remains a state of art, primarily since such reads are highly prone to errors. Previous attempts to use Nanopore reads for analyzing D4Z4 region showed only a limited success. One of the main challenges is the lower coverage of the current Nanopore platform in comparison to other sequencing platforms. Enrichment step is required to reach appropriate read depth. In addition, no effective workflow exists for handling the sequencing data. In the project an enrichment protocol can first be optimized for targeting the D4Z4 array as well as other sequences that are relevant to molecular diagnosis.

Example 2

Using a CRISPR/Cas9 Approach to Enrich the D4Z4 Array on Chromosome 4

A CRISPR/Cas9-based enrichment protocol was developed to specifically characterize D4Z4 arrays from chromosome 4 by Nanopore long-read sequencing. Briefly, after DNA extraction, 5' ends were dephosphorylated to reduce ligation of sequencing adapters to non-target DNA fragments. Cas9 ribonucleoprotein particles (RNPs), with bound crRNA and tracrRNA were added to the DNA samples. The targeted region (e.g. D4Z4 arrays) was cut by the CRISPR/Cas9.

The dsDNA cleavage by Cas9 revealed blunt ends with ligatable 5' phosphates.

Afterward, a dA-tail was added to the DNA fragments, which prepared the blunt ends for sequencing adapter ligation. However, only the targeted fragments were both 3' dA-tailed and 5' phosphorylated, therefore the sequencing adapters were ligated primarily to Cas9 cut sites which allowed sequencing of the fragments.

Long-read sequencing was done using the Nanopore sequencer following the manufacturer's protocol.

D4Z4 array on chromosome 4 was targeted using a gRNA specifically recognize a region ~3 kb upstream of the D4Z4 array. The sequence was specific to the D4Z4 array on chromosome 4 therefore only the chromosome 4 alleles were targeted and enriched for sequencing.

Various software and workflows were used to analyze the data. Each received different numbers of hits. For example. 83 reads were identified when the BWA-MEM was used to identify reads with both the p13E11 (the sequence is approximately 2 kb upstream of the D4Z4 array) and D4Z4 sequences.

FIGS. 3A-3B show two of the long-reads containing the target region. One (FIG. 3A) 82 kb-long read contains 8 D4Z4 repeat and the flaking regions, which is in concordance with the known repeat size of this sample. The read in FIG. 3B is 102 kb and contains 32 repeat, which represents the unaffected allele.

Atypical methylation found in an early onset FSHD clinical cohort: While most of the individuals affected by FSHD show the first clinical signs later in life (late teens, early adulthood or later), a small percentage (4-21%) of patients develop muscle weakness before 10 years of age. These patients with early onset FSHD tend to have fewer than average number of the D4Z4 repeating units for typical FSHD1, more severe muscle weakness, younger age at loss of independent ambulation, and a greater risk of having non-muscle manifestation. However, the correlation between disease severity and D4Z4 repeat number was inconsistent, indicating involvement of other genetic and environmental modifiers.

Factors affecting epigenetic status, such as histone post-translational modifications, chromatin remodeling proteins, long non-coding RNAs, and DNA methylation, were altered in the D4Z4 macrosatellite repeat region in FSHD.

These changes of epigenetic state cause transcriptional de-repression of the DUX4 gene which is located in the D4Z4 repeat array.

Among the factors, DNA methylation has been extensively studied. Family cohorts of individuals with FSHD1 who were either clinically affected or asymptomatic were investigated and it was found those affected with FSHD1 had hypomethylated DNA, while healthy controls had significantly more methylation. Intermediate levels of DNA methylation were found in asymptomatic FSHD subjects. This work indicated that epigenetic stability of repression, correlating with DNA methylation status at the distal D4Z4 repeat, reflects the extent an individual with FSHD1 is affected by the disease.

Recent reports showed that SMCHD1 is also a genetic modifier of FSHD1 severity in adults. Patients with FSHD1 developed more severe disease phenotypes when they carry certain mutations in SMCHD1.

In addition, mutations in the DNMT3B gene were also reported to modify disease severity and may be responsible for some cases of FSHD2.

Based on these findings, it was determined that the DNA methylation level in the early onset FSHD1 cohort is lower than adult onset FSHD1 and that disease severity correlates with the DNA methylation level in this cohort. In addition, some patients, especially those with a more severe disease phenotype have mutations in additional genes further modifying disease severity.

In a multicenter collaborative study on the clinical features and quality of life of early onset FSHD, 53 participants with early onset FSHD1 were recruited and enrolled. Participants were included based on a genetically confirmed contraction of the D4Z4 repeat array, ranging from 1-10 D4Z4 repeating units ("RUs") at chromosome 4q35. Additional inclusion criteria included onset of facial weakness at less than 5 years of age or onset of shoulder girdle weakness at less than 10 years of age. The onset of facial muscle weakness was validated by reviewing the old videos or photos with the clinical examiner at the time of enrollment. Of the 53 affected participants, 60% are female and 40% are male. The average age at enrollment was 22.9 (SD 14.7, range 3.0-56.8) years. The mean size of the contracted 4qA D4Z4 allele was 3.4 (SD 2.1) RUs and 77% of participants had 4 RUs or fewer. Since there is a rough inverse correlation between the D4Z4 repeat number and disease severity, it was not surprising that the majority of the participants had smaller numbers of D4Z4 RUs in their contracted array. However, roughly 30% of participants have larger D4Z4 size from 5-10 D4Z4 RUs.

The DNA methylation status of the distal-most pathogenic D4Z4 RU (FSHD1 assay) was analyzed and the total D4Z4 methylation status (FSHD2 assay) in five of the participants.

An atypical DNA hypomethylation state was found that was significantly less methylated than what is typically found in classical FSHD1 subjects but not to the extent across all D4Z4 arrays as found in typical FSHD2 (FIG. 2)

These data indicate that early onset FSHD maintains the epigenetic component characteristic of FSHD (part of the spectrum of the FSHD), however, the pathogenic mechanism is likely distinct from both FSHD1 and FSHD2.

It is worth noting that the assay only examines the DNA methylation pattern in the last repeat. The long-read sequencing assay can provide detailed information regarding the repeat numbers as well as DNA methylation states. It can characterize a unique cohort and investigate mechanisms contributing to this severe form of childhood FSHD, thereby providing potential diagnostics and new targets for therapeutic development.

Example 3

Development of a Nanopore Long-Read Sequencing Assay to Evaluate the D4Z4 Arrays on Both Chromosome 4 and Chromosome 10 and Build a Data Analysis Workflow.

A CRISPR/Cas9-based enrichment protocol was developed to specifically select the D4Z4 array from chromosome for Nanopore long-read sequencing. This protocol was configured so the D4Z4 array on both chromosome 4 and 10 could be assayed at the same time. Nanopore recommends design of multiple gRNAs that target multiple targets in an assay. Additional gRNAs were added that target other genomic regions that are relevant to FSHD diagnosis, including the polyadenylation signal as well as known causative genes for FSHD2.

Example 4

Improvement of the Protocol that Enriches the D4Z4 Region in Genomic DNA for Long Read-Sequencing Using the Nanopore Sequencer.

Before the CRISPR/Cas9-based enrichment protocol was developed, several different approaches to enrich the D4Z4 region were tested in order to increase coverage, including targeted amplification using high fidelity enzyme, Φ29 DNA polymerase with primers specifically targeting the region; sequence-specific probe hybridization and various size-selection approaches.

The inventors recognized from the resulting data that none of the approaches effectively enriched the D4Z4 sequences, except the CRISPR/Cas9-based enrichment protocol.

DNA is isolated from FSHD myoblasts then was blocked from ligation with the adaptors during library preparation.

Figure 4:
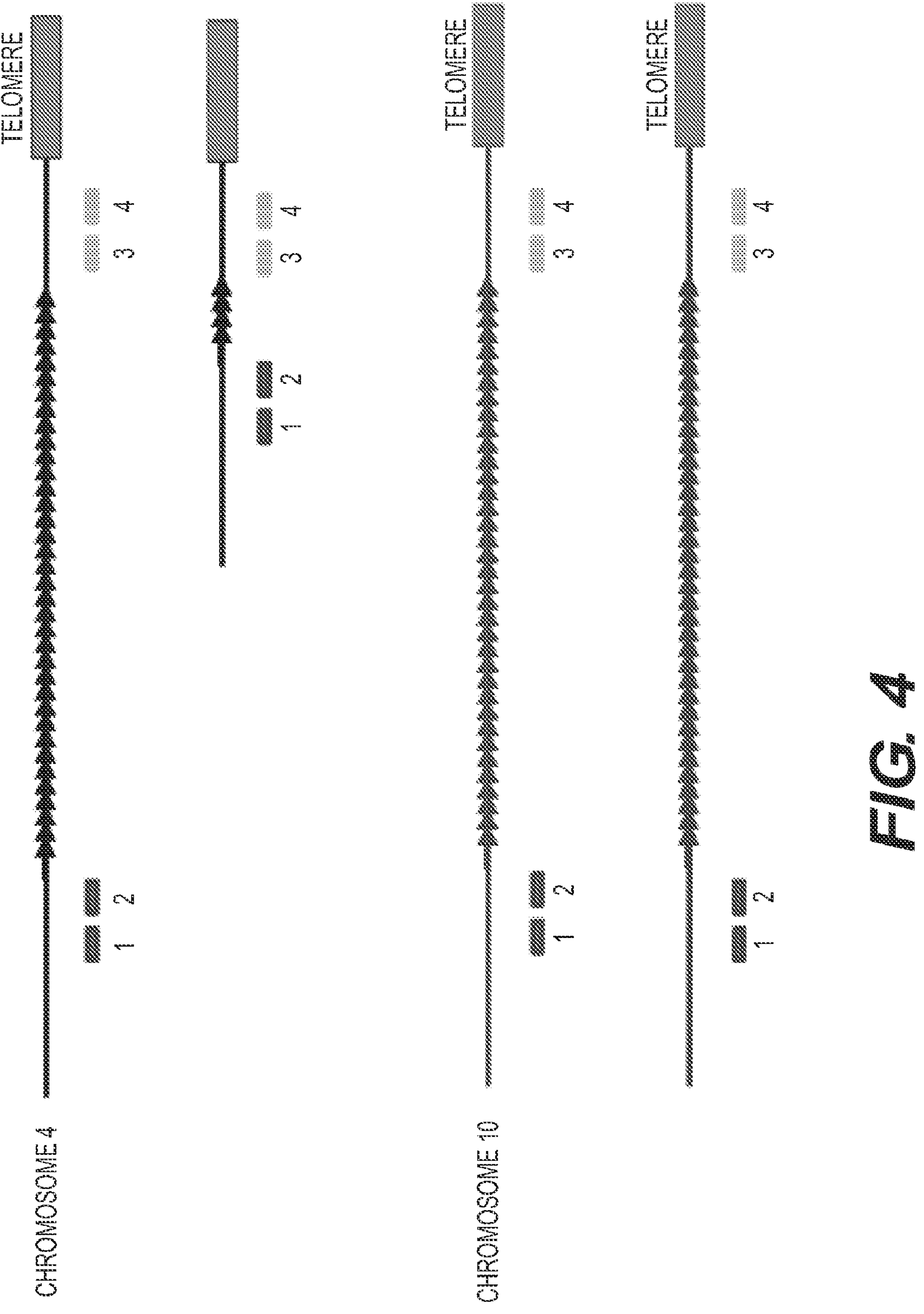
FIG. 4 depicts guide RNAs 1 and 2 (red, left) and 3, 4 (green, right) that were designed to target the D4Z4 arrays on chromosomes 4 and 10. The same principles were used to obtain DNA regions of interest from the SMCHD1, DNMT3B and LRIF1 gene regions with the other gRNAs disclosed herein.

The region of interest (D4Z4 array on chromosome 4 and 10) was targeted using a gRNA specifically recognize the region upstream and downstream of the D4Z4 array. As shown by FIG. 4, probes 1 and 2 target the region upstream of the D4Z43 array and probes 3 and 4 target the downstream region at the end of the array.

Figures 8, 9:
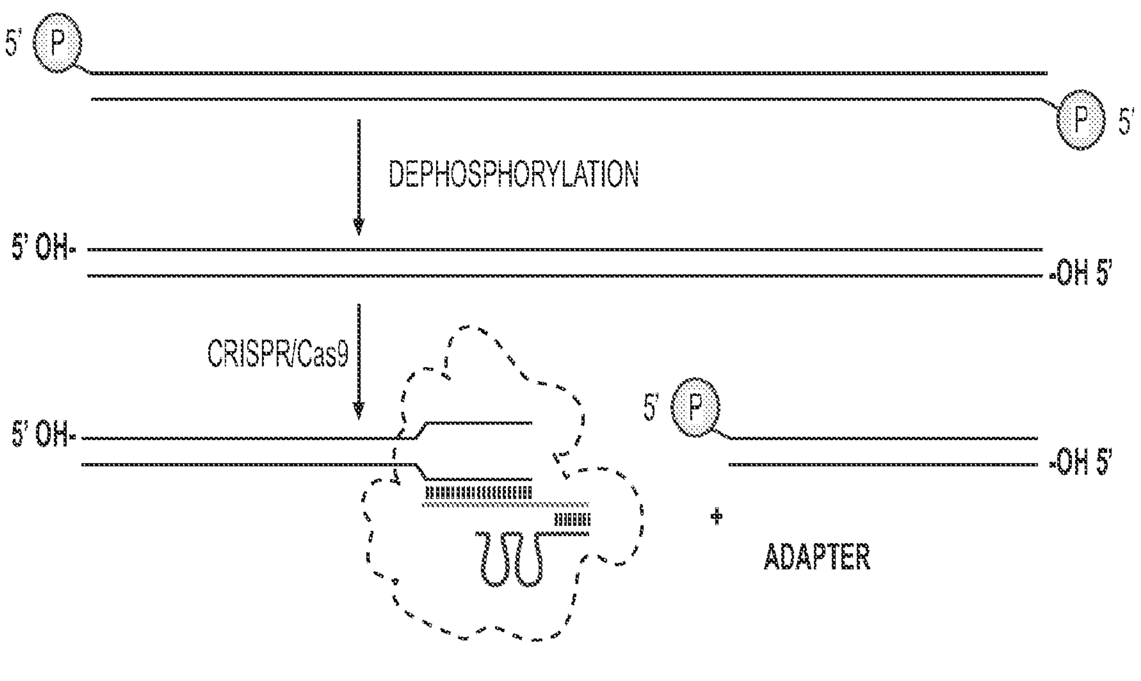
FIG. 8 illustrates 5' dephosphorylation and processing of the dephosphorylated polynucleotide by CRISPR/Cas9 in presence of a 5' phosphorylated, commercially-available adapter.
FIG. 9 illustrates enrichment of sequence of interest using two guide RNA instead of one shown in FIG. 8, which increase efficiency of the enrichment. The method will enrich DNA fragments that encompass the targeted region (lower, green or contain the targeted region plus additional sequence beyond the region (upper, red)

The targeted sites were cut by CRISPR/Cas9 specifically, see FIGS. 8 and 9.

The freshly cut sites were able to be ligated with the adaptors and the genomic region was enriched and sequenced. The D4Z4 region on chromosome 4 and 10 was successfully enriched in the study.

Ligation Sequencing Kit (SQK-LSK109) with enrichment of specific genomic regions using CRISPR/Cas9-enrichment protocol can be used for the proposed studies as described in the data.

Long-read sequencing was done using the Nanopore sequencer following the manufacturer's protocol. The data produced provided more information about the D4Z4 arrays, including the size and methylation state of the reads.

One advantage of performing long-read sequencing using the Nanopore technology is that the sequencing data contain DNA methylation information when proper informatics tools are used to analyze the data. Such epigenetic information would be lost by simple PCR amplification of the target or region of interest. DeepSignal and additional tools were used to analyze the long-read data to determine the DNA methylation state of the region.

Example 5

Development of a Bioinformatics Pipeline for Handling Long-Read Sequencing Data and Analysis of D4Z4 Repeat Sequences therein.

Existing bioinformatics tools may be applied to the analysis of the features of long-read sequencing data. In particular, both de novo assembly and reference-based read mapping approaches are explored for identifying D4Z4 regions in the sequencing reads.

For de novo assembly, applicability of modern Nanopore assemblers, including Canu, Miniasm, Wtdbg2, and FLYE, are explored using their error correction abilities when available.

For read mapping with DUX4 reference, applicability reads alignment/mapping tools, such as LAST, Minimap2, NGMLR, are explored for searching DUX4 reference sequence within the sequencing reads or assembled contigs.

Appearance of DUX4 instances are analyzed within the identified reads. For reads that cover all D4Z4 repeats (i.e., contain flanking sequences), DUX4 are searched within such reads.

When reads overlap with D4Z4 only partially, such reads are aligned and/or assembled to obtain contigs that contain all D4Z4 repeats.

In addition to DUX4, sequences that are unique or relatively unique to the regions such as p13E11 and 4qA and B specific sequences are used as references for searching. The resulting pipeline includes visualization of the analysis results via Integrative Genomics Viewer enabling users to better understand of the data and clearly see its major features. Additional scripts written using Python were used fir data analyses and visualization.

Example 6

Validation of the Long-Read Sequencing Approach Using DNA Samples from the Recent Study of Early Onset FSHD.

DNA methylation levels and patterns in the D4Z4 region were associated with different disease states and types of FSHD. While FSHD1 had DNA hypomethylation only on the contracted allele, the FSHD2 is hypomethylated on all D4Z4 repeating units of 4q and 10q alleles. The data showed that low DNA methylation at the last D4Z4 repeat, similar to that of compound FSHD1 and FSHD2, were found in early onset FSHD, indicating additional factors affecting the DNA methylation level in these subjects and contribute to the early disease onset and more severe clinical presentations. 68 samples (48 FSHD and 20 control) on hand were examined to determine whether this unique methylation pattern is common in this cohort or separates into informative groupings to determine how the DNA methylation status correlates with clinical symptoms such as muscle weakness, disease onset and severity) and molecular features like D4Z4 repeat number of patients.

Example 7

Determination of D4Z4 Repeat Size and DNA Methylation Status of the FSHD Samples and Samples from Unaffected Individuals Using Long-Read Sequencing Approach.

Forty eight FSHD and 20 control samples are screened using the long-read sequencing assay developed herein. High molecular weight DNA is isolated from peripheral blood mononuclear cells (PBMCs) and the long-read sequencing is conducted as described herein. The results are compared to the D4Z4 repeat size data obtained during the clinical study, which were determined by standard genetic testing. In addition to validating the repeat number, the DNA methylation status of each of the D4Z4 both chromosome 4 and 10 is determined. This method allows direct examination of each repeat in the D4Z4 arrays. The data showed atypical DNA methylation patterns in samples from patients with early onset FSHD. The data from patients' PBMCs provide insights of whether this is true in all patients' cells or only a specific sub-population. Data from the control samples are used to identify threshold for normal level of methylation in the D4Z4 region.

Example 8

Investigation of the Role of Epigenetic Changes in D4Z4 Region in FSHD Inset and Severity.

Clinical data from the study cohort including, age of onset, disease severity score, manual and quantitative muscle measurements and muscle functional tests are collected and analyzed. Repeat numbers do not correlate with disease severity after the data are adjusted for age and gender in this patient cohort. Rather methylation state or a combination of the repeat size and methylation state correlated with the clinical parameters.

DNA methylation levels associate with various clinical and motor evaluations in order to determine whether the DNA level is associated with a clinical disease phenotype. The measurements include timed function assessments (e.g., a 6-minute walk), quantitative muscle testing, manual muscle testing, and FSHD clinical severity score. Interactions between the methylation status and gender as well as the size of D4Z4 repeat array, specifically, whether longer repeat array is associated with higher methylation level in this cohort can be analyzed. Associations between methylation status and other characteristics can be performed in the 48 early onset FSHD cases. These associations can use methods appropriate for the data types. In addition to the correlation analyses between methylation levels and clinical phenotypes, samples are grouped to two groups (FSHD1 and FSHD1+FSHD2) based on the methylation pattern in case distinct differences are observed among individuals in this cohort. Clinical phenotypes between the two groups can be compared to determine the differences. Methods used are appropriate for the type of data, i.e. student's t-tests for data that are normally distributed, Wilcoxon non-parametric tests for those that are not. Although larger D4Z4 arrays (more RUs) are usually associated with milder disease, 30% (n=14) participants in this study have 5 or more repeats. Considering the early onset of the disease, low DNA methylation level and potential FSHD1+FSHD2 methylation pattern in the D4Z4 repeat region are observed from these individuals.

Example 10

Long-Read Sequencing with CRISPR/Cas9 Enrichment for Investigating Repeat Number and DNA Methylation of the D4Z4 Region CRISPR/Cas9 gRNA Design. Guide RNAs were designed using tools available at crispr.mit.edu and CHOPCHOP. For the upstream guide RNA (gRNA), a DNA sequence from the P13E11 region was used and the highest scoring forward facing gRNAs were selected. For the downstream guide, a DNA sequence from the pLAM region was used and the highest scoring reverse gRNAs were selected.

Single guide RNAs (sgRNA) from IDT were used. These sgRNAs combined the tracrRNA and crRNA duplex into one RNA using a linker sequence. IDT Alt_R protocols are incorporated by reference to hypertext transfer protocol secure//sfvideo.blob.core.windows.net/sitefinity/docs/default-source/protocol/alt-r-crispr-cas9-protocol-in-vitro-cleavage-of-target-dna-with-rnp-complex.pdf?sfvrsn=88c43107_24 (last accessed May 24, 2021).

DNA sample preparation. High molecular weight DNA was extracted using Nanobind CBB Big DNA Kit (Cells, Bacteria, Blood) according to the manufacturer's protocol. Briefly, pelleted cells ($1\times10^6$-$5\times10^6$) were resuspended in PBS. 20 ul proteinase K and 20 ul CLE3 were added to the cells. The sample was incubated at 55° C. for 10 minutes. Then 200 ul BL3 was added and sample incubated at 55° C. again for 10 min. The Nanobind disk was added to the sample followed by addition of 300 ul isopropanol and mixing by inversion. The tube was placed on a magnetic rack and washed with 700 ul CW1 once, followed by 500 ul CW2 twice. DNA was eluted from disk with 75 ul EB. The elutate was pipetted 10 times with narrow bore pipette and left at room temperature overnight.

All DNA samples were used within a week of extraction, except the sample from patient sample #3. The high molecular weight DNA sample from patient #3 was isolated approximately one year ago and stored at 4° C.

Nanobind materials and methods are incorporated by reference to hypertext transfer protocol secure://15a13b02-7dac-4315-baa5-b3ced1ea969d.filesusr.com/ugd/5518db_c4d6d1aa423342828ad504d0264e0f8f.pdf?index=true (last accessed May 24, 2021).

Long read sequencing. Preparation of sequencing libraries were done according to Oxford Nanopore Technology's CRISPR/Cas9 enrichment protocol using the SQK LSK-109 kit or the SQK-CS9109 protocol and kit. Sequencing was performed on MinION flowcells (v 9.4.1) using a MK1C or MinION device. CRISPR Cas9 enrichment materials and methods are incorporated by reference to hypertext transfer protocol secure://community.nanoporetech.com/protocols/cas9-targeted-sequencing/v/ENR_9084_v109_revP_04Dec2018 (last accessed May 24, 2021).

Identifying Target Reads. Accelerated base-calling was performed on an ubuntu computer with a compatible graphics card using a GPU compatible version of GUPPY (Linux 64-bit GPU v4.5.4). Base-calling was performed using the guppy_basecaller script with the appropriate kit and flowcell information using high accuracy base-calling settings to generate FASTQ files.

Reads from the FASTQ files generated by base-calling were aligned using bwa mem with default settings and a single D4Z4 repeat as the reference sequence. The resulting sam file output was filtered for reads that were successfully aligned using samtools view -b -F 4, where -b outputs the results in bam format and -F 4 filters out reads with the 0x0004 flag, which indicates that the read is unmapped. The resulting bam file was converted to a FASTQ file using samtools fastq. The resulting FASTQ files for each nanopore run were merged for downstream analysis. Guppy instructions are described by, and incorporated by reference to, hypertext transfer protocol secure://community.nanoporetech.com/protocols/Guppy-protocol/v/gpb_2003_v1_revs_14dec2018/modified-base-calling.

The reads that aligned to D4Z4 were aligned in series to several sequences immediately flanking the repeat array to identify its allele and structure, and filtered using the same methods described above. These flanking sequences included the P13E11 region upstream of the repeat array (350 bases), the 4qA specific sequence (pLAM) (250 bases), and a 4qB specific sequence (173 bases). Reads that only aligned to D4Z4 and P13E11 or D4Z4 and 4qA/4qB were considered to be partial arrays.

To determine the number of D4Z4 repeats that were identified, each secondary D4Z4 alignments was counted as a repeat. Reads that contained all three regions (P13E11, D4Z4, and 4qA/B) were considered to be a complete repeat array. Only when a complete repeat array had a repeat count <10 it was considered contracted while a full or partial repeat array longer than 10 repeats was considered to be normal.

Distinguishing between Chromosome 4 and Chromosome 10 sequences. Reads that contained BlnIrestriction sites were considered to be from Chromosome 10. Reads that contained XapI (ApoI) restriction sites were considered to be from Chromosome 4. Reads that contained a mixture were considered to contain a mixture of chr10 and chr4 repeats. Since both XapI and BlnI restriction sites are palindromic, the strand of the reads was not considered during the search.

Analysis of methylation. Base-calling of modified bases was also completed with GUPPY (Linux 64-bit GPU v4.5.4) using a configuration file specifically for calling base modifications. Methylation data saved to the outputted fasts file were extracted using ont-fast5-api. Individual reads were grouped by the number of D4Z4 repeats that were identified and a multiple sequence alignment (MSA) was performed using MUSCLE (v3.8.31). Methylation probabilities were overlaid on this MSA and the results were displayed using a custom python script.

CRISPR Cas9 Enrichment Long-Lead Protocol Allows Direct Counts of the D4Z4 arrays. The inventors sought to obtain long reads that covered the entire D4Z4 region, which would allow determination of the number of the repeats.

To achieve this objective, sgRNAs used to cut the DNA were located in the p13E11 and pLAM regions (FIG. 13) to encompass the whole D4Z4 array. A complete D4Z4 array fragment was defined by a fragment that contains both upstream and downstream sequences that flank the D4Z4 array, thus the numbers of the repeat units could be correctly determined. Genomic DNA from immortalized human myoblasts and peripheral blood mononuclear cells (PBMCs) were examined.

Without enrichment, we were not able to obtain any read that contained the complete D4Z4 fragment.

Figures 10A, 10B, 10C, 10D:
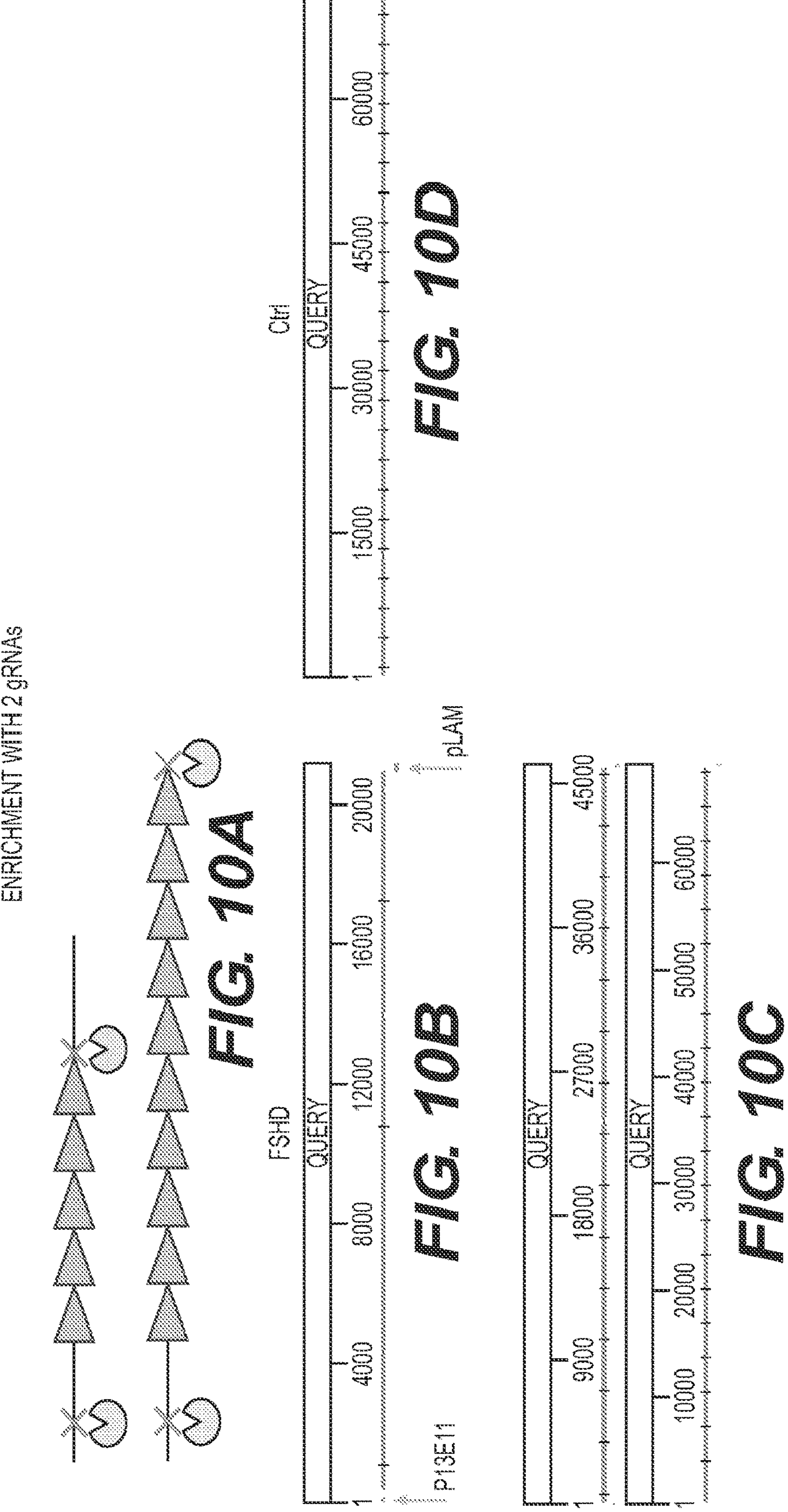
FIG. 10A illustrates that the guide RNAs are flanking the target D4Z4 region, including contracted and unaffected alleles.
FIG. 10B depicts use of the two-guide approach, where the affected allele (6 D4Z4 RUs) was detected in a patient's sample.
FIG. 10C shows detection of two unaffected D4Z4 arrays in the cells from a FSHD patient.
FIG. 10D describes the D4Z4 array in a non-FSHD control subject who is a sibling of the patient.

Using the CRISPR/Cas9 enrichment protocol, we were able to detect the contracted alleles in cells from all FSHD samples tested, see FIG. 10.

For FSHD sample #1, the contracted allele contains 4 D4Z4 repeat units.

In addition to the contracted allele, we also detected a healthy allele with 18 repeat units.

Three alleles with full D4Z4 region were detected in the FSHD sample #2, the contracted allele contains 6 repeat units (10 reads) and the healthy alleles are 14 repeat units (1 reads) and 21 repeats (1 read).

CRISPR Cas9 Enrichment Long-Lead Protocol Allows Detections of the D4Z4 arrays in PBMCs from patients with FSHD. Peripheral blood mononuclear cells (PBMCs) from patients with FSHD were used to evaluate the proposed protocol when used on clinical samples with limited materials. PBMCs from three patients were collected from a clinical study of early onset FSHD. The patients were diagnosed to have FSHD1 based on genetic testing using southern blotting assay.

All the contracted alleles were identified using the CRISPR/Cas9 enrichment long-read protocol.

In addition, we detected the other normal alleles, including those on chromosome 10.

Figure 13:
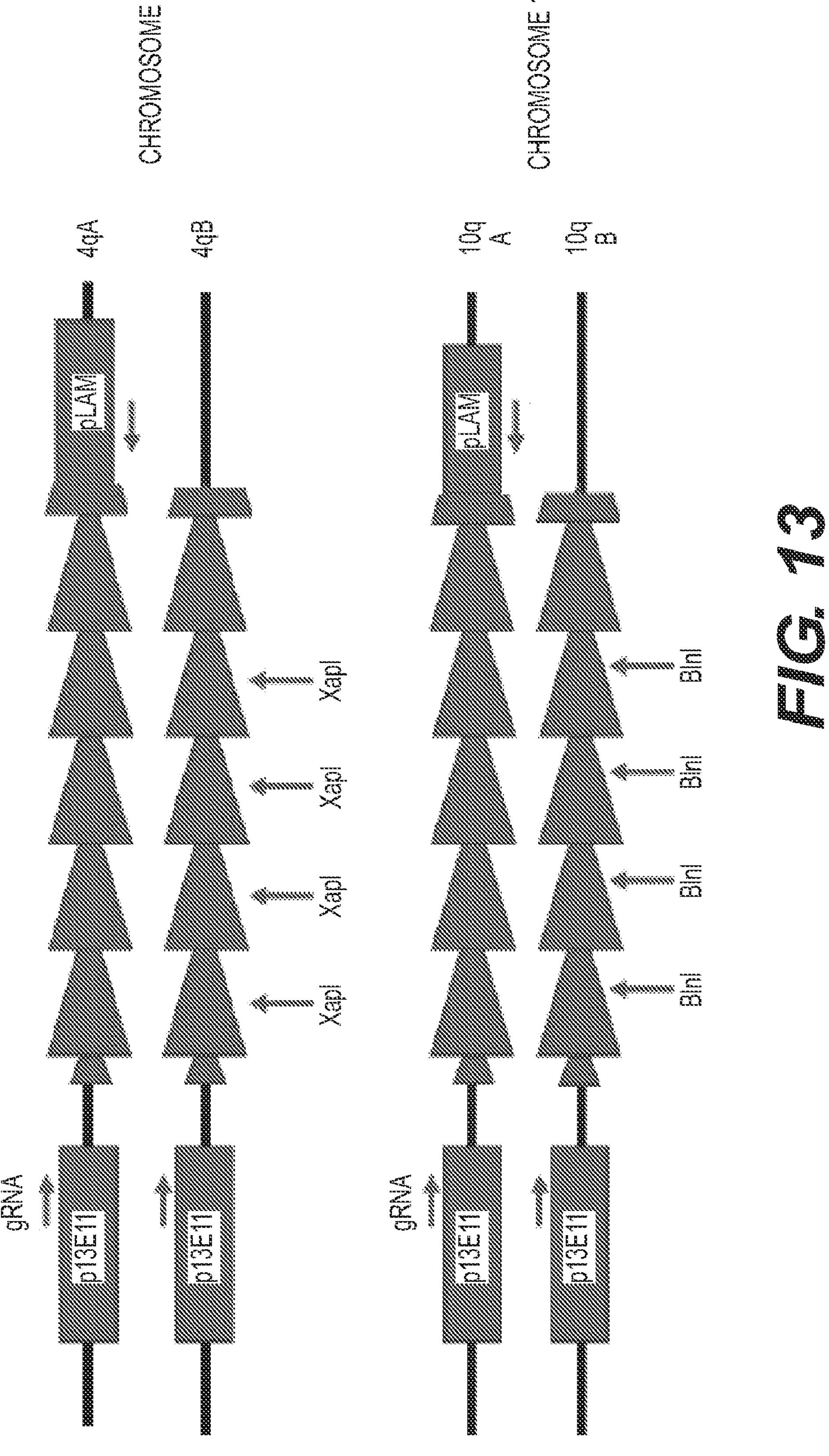
FIG. 13 describes guide RNAs located in the p13E11 and pLAM regions to encompass the whole D4Z4 array. A complete D4Z4 array fragment is defined by a fragment that contains both upstream and downstream sequences that flank the D4Z4 array, thus the numbers of the repeat units and methylation in each repeat can be correctly determined.

Hybrid D4Z4 Arrays Containing D4Z4 unit from the Chromosome 4 and 10 can be Identified via Chromosome-Specific Sequences. In order to separate alleles from chromosome 4 and 10, we used the restriction enzyme sites that are specific to each chromosome to distinguish the alleles (FIG. 13).

Figure 12:
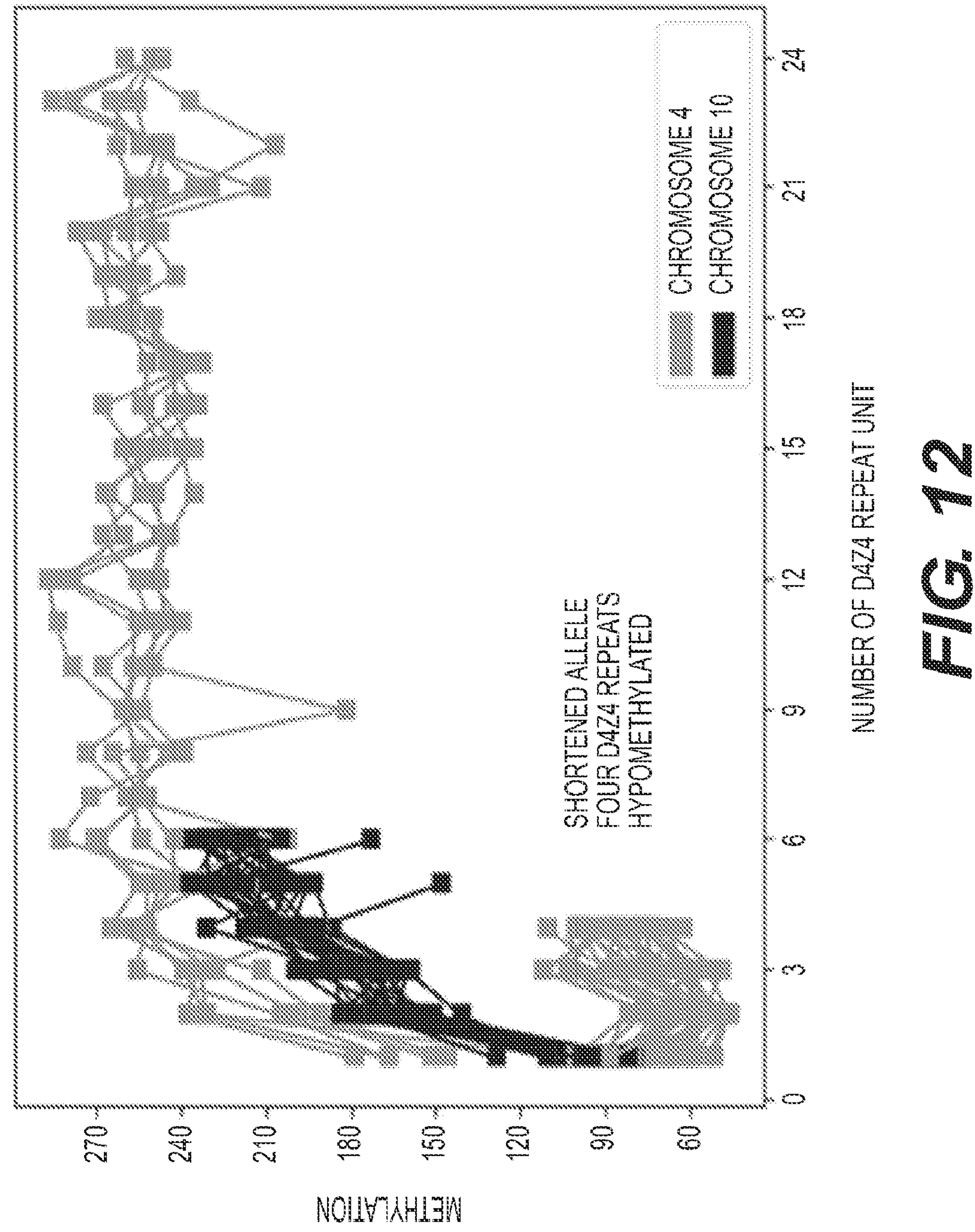
FIG. 12 describes DNA methylation in D4Z4 arrays from muscle cells of a patient with FSHD. Two D4Z4 arrays from chromosome 4 and one from chromosome 10 were detected. The DNA molecules were hypomethylated in the D4Z4 repeats in the contracted chromosome 4 allele but not the other chromosome 4 D4Z4 array that are longer (24 repeat units). The lower cluster of values (grey grouping at the bottom left) depicts methylation of 4 D4Z4 repeats from a contracted allele. The longer chromosome 4 allele (grey at the top) is not hypomethylated The allele from chromosome 10 is not hypomethylated.

FIG. 12 shows the allele from chromosome 10 can be clearly separated from chromosome 4.

DNA Methylation Levels are Different in Individual Repeats in the D4Z4 Region. Previous studies showed that the DNA in the D4Z4 region is hypomethylated in FSHD independent from the primary genetic mutations. Status of DNA methylation of the D4Z4 region can provide additional information on the disease state.

The DNA methylation of each D4Z4 is determined by counting methylated cytosines in each of the repeat. The results showed that DNA methylation was lower at the D4Z4 repeat units that were closer to the p13E11 and gradually increase into the later repeat units. When an allele was contracted, the methylation was much lower in comparison to the healthy allele (FIG. 12).

In addition to the length of the D4Z4, additional gene regions can be sequenced and mutations identified using additional guide RNAs that encompass the causative genes of FSHD2, including SMCHD1 (structural maintenance of chromosomes flexible hinge domain containing 1), DNMT3B (DNA Methyltransferase 3B) and ligand-dependent nuclear receptor-interacting factor 1 (LRIF1).

It is challenging to sequence and assemble large repeats using current NGS technologies since the reads are too short to span the entire repeat array. DNA assemblers and aligners depend on unique sequences to properly place reads so properly placing reads in a repetitive region can be difficult if not impossible. However, long read sequencing technology like Oxford Nanopore and Pacific Biosciences can produce reads that span 10 s-100 s kb, long enough to sequence an entire D4Z4 repeat array. However, Nanopore sequencing sequences native DNA so it can distinguish base modifications such as CpG methylation which is important for FSHD development. With the long reads of ONT sequencing, distinguishing the methylation states of different repeats in the array become possible for the first time.

Since the repeat array length is highly variable, it is not feasible to attempt to align reads to a reference repeat array. Instead, aligning nanopore reads to landmark sequences of interest like the D4Z4, P 13E11, and 4qA/B allele sequences allows rapid identification of reads containing D4Z4 repeat arrays. In the alignment step, the Burrows-Wheeler Aligner (bwa) can be substituted with other aligners such as minimap2, BLAST, or any other suitable or equivalent aligners. Our results showed that CRISPR/Cas9 targeted nanopore sequencing successfully.

Distinguishing between 4qA and 4qB alleles is important for the proper diagnosis of FSHD. The 4qA allele contains a polyadenylation signal that permits formation of stable DUX4 transcripts. The 4qB allele is not known to cause FSHD. Further description of intact poly-A sequences are described by, and incorporated by reference to, 4. Lemmers, R. J., et al., *A unifying genetic model for facioscapulohumeral muscular dystrophy*, Science. 2010, 329, 1650-3; and to Dixit, M., et al., DUX4, a candidate gene of facioscapulohumeral muscular dystrophy, encodes a transcriptional activator of PITX1, Proceedings of the National Academy of Sciences of the United States of America. 2007, 104, 18157-62.

Example 10

Figure 5:
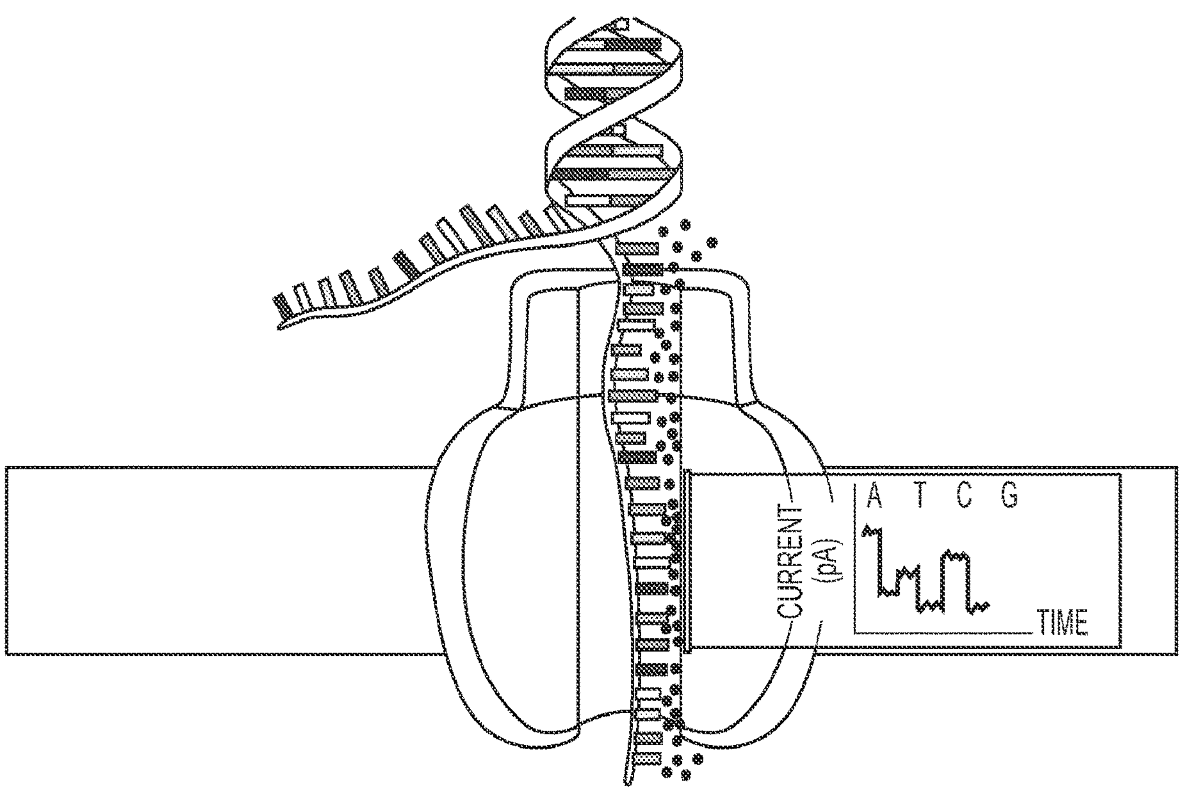
FIG. 5 structurally depicts nanopore sequencing and the sequence data produced.
Figure 6:
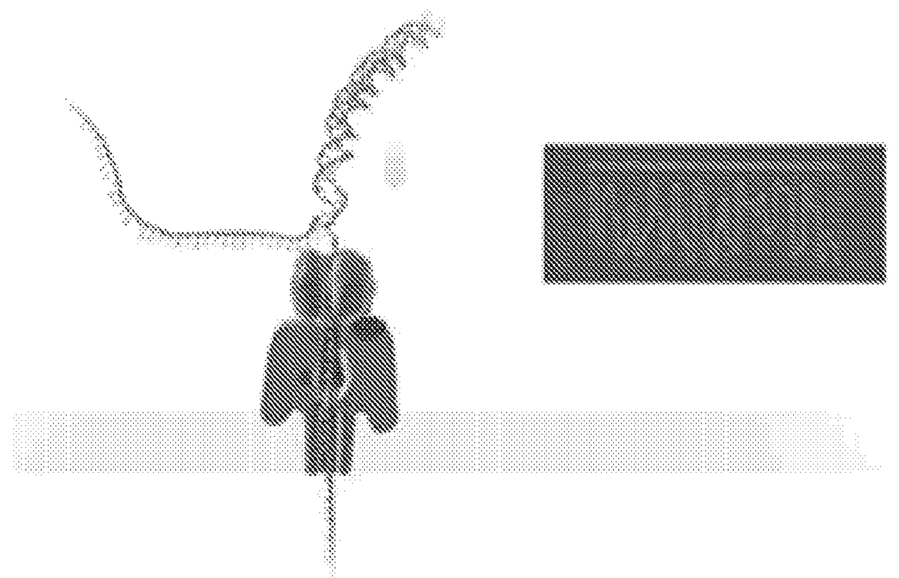
FIG. 6 also structurally depicts nanopore sequencing and resulting sequence data.

This example describes nanopore sequencing and data obtained from it in detail. As shown by FIG. 5. A single strand of a DNA to be sequenced is pulled through a nanopore (protein pore). Each nucleotide base affects ion movement (FIG. 5, black dots) through the pore to a different degree. Current (pA) is measured as each nucleotide or methylated nucleotide base passes through the pore and as shown in the graph on the right side of FIG. 5. Differences in current identify each nucleotide base thus sequencing the DNA. FIG. 6A also illustrate this sequencing mechanism. As disclosed herein the D4Z4 array obtained from a methylated nucleotide bases.

Figure 7:
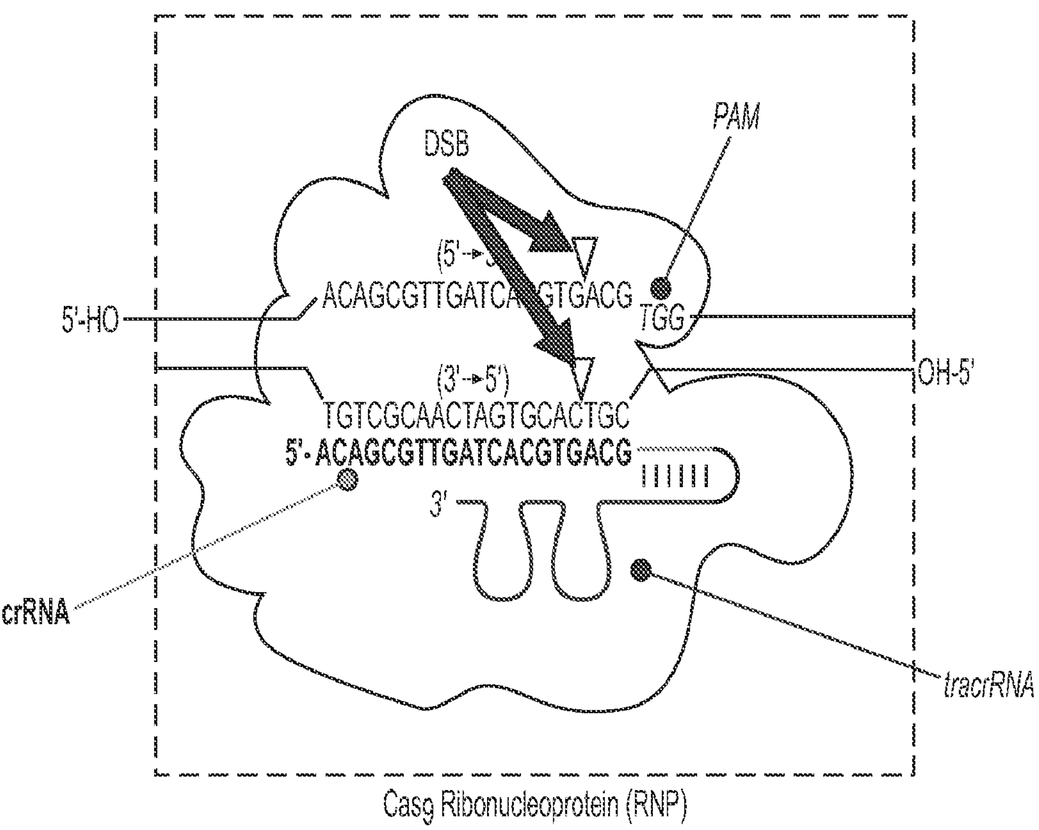
FIG. 7 illustrates use of Cas9 ribonucleoprotein. DSB: double strand break; PAM: protospacer adjacent motif; tracrRNA: trans-activating crispr RNA; crRNA: CRISPR RNA.

The efficacy and efficiency of nanopore sequencing of the D4Z4 array is enhanced by enrichment of the D4Z4 DNA from a biological sample. The enrichment process is illustrated by FIGS. 7-9. The CRISPR/Cas9 elements are similar to, and adapted from, those of a bacterial immune system. Guide RNA directs Cas9 to a specific DNA sequence to be cut. Cas9 protein cuts at the specific site, causing a double stranded cut or break; see FIGS. 7 and 8. FIG. 8 also shows the addition of commercially available sequencing adaptors to the enriched D4Z4 sequences. By selecting guide RNAs (gRNAs) that cut DNA sequences flanking the targeted D4Z4 repeat array (FIGS. 9 and 10A-10D) a enriched preparation of DNA containing the D4Z4 repeat array is produced which is then sequenced using a nanopore sequence method. D4Z4 regions of different lengths or from different subjects or patients are enriched and subsequently characterized by nanopore sequencing which in addition to a D4Z4 array length determination provides methylation profiles for the sequenced enriched DNAs.

Figure 11:
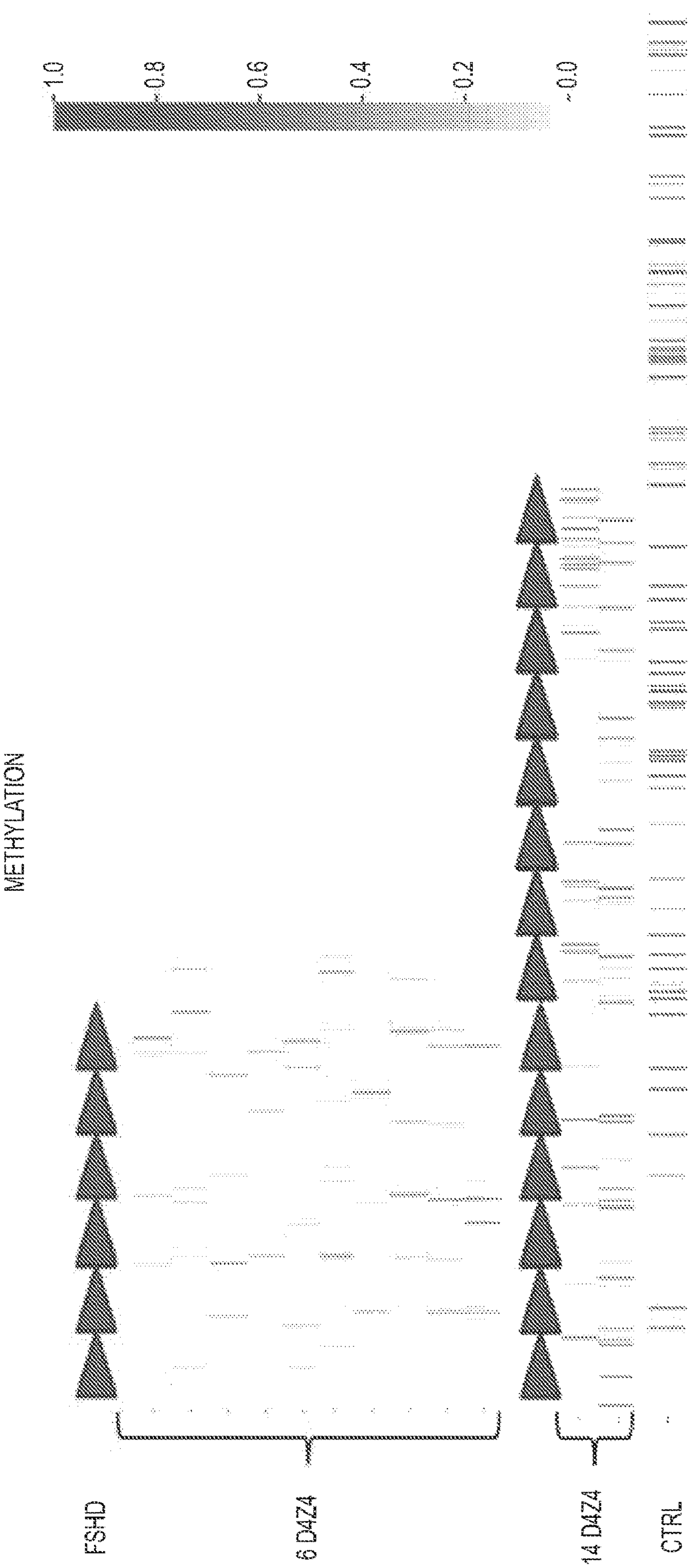
FIG. 11 describes methylation patterns in a patient with FSHD (6 repeats in D4Z4 array as shown by six arrows at the top; and methylation patterns of the other allele having 14 repeats in D4Z4 array (14 D4Z4), and control (Ctrl). The scale on the right indicates by intensity (top red/dark gray to bottom light pink/light gray) the degree of methylation.

Methylation patterns are obtained from the enriched D4Z4 array DNA that has been sequenced, see FIG. 11 which describes methylation patterns of the D4Z4 region of a contracted allele in a patient with FSHD (6 repeats in D4Z4 array as shown by six arrows at the top); and methylation patterns of an unaffected allele with 14 repeats in the D4Z4 array (14 D4Z4), and control (Ctrl). Detection of hypomethylation of a contracted (shortened) D4Z4 allele helps diagnose FSHD, see FIG. 12. The lower cluster of values (grey) describes methylation of 4 D4Z4 (FSHD) on chromosome 4, while the unaffected allele on chromosome 4 (gray at the top) is not hypomethylated. The D4Z4 array on chromosome 10 is not hypomethylated.

As shown herein, a cost-effective long-read sequencing based assay has been designed and developed that can determine repeat number and DNA methylation of the D4Z4 region for diagnosis of FSHD. This method employs a CRISPR/Cas9-based enrichment protocol in combination with the Nanopore long-read sequencing to specifically target and enrich DNA from the D4Z4 region. gRNAs were designed to target regions upstream and downstream of the D4Z4 array. This procedure successfully sequenced complete D4Z4 arrays allowing their relative lengths to be determined. Additional guide RNAs were designed to target other genetic regions that are involved in FSHD2.

This method provides a quick and inexpensive way to comprehensively determine D4Z4 array length and methylation profiles which correlate with FSHD1 and methylation profiles and mutations in other genes associated with FSHD2.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

What is claimed is:

1. A method of diagnosing Facioscapulohumeral muscular dystrophy (FSHD) in a subject, comprising:

screening for Facioscapulohumeral muscular dystrophy type I (FSHD1) by performing nanopore long-read sequencing on a nucleic acid sample from the subject which has been enriched for DNA sequences comprising a D4Z4 repeat array using CRISPR/Cas 9 and guide RNA comprising SEQ ID NO 1 and SEQ ID NO 2 which recognize DNA sequences flanking the D4Z4 repeat array;

measuring a number of D4Z4 repeats in the D4Z4 repeat array and/or measuring a methylation of bases in a FSHD permissive allele; and identifying a subject having FSHD1 when ten or fewer D4Z4 repeats are detected in the D4Z4 repeat array or when ten or fewer D4Z4 repeats are detected and when the permissive allele of the subject are hypomethylated compared to that in a normal control subject not having FSHD1.

2. The method of claim 1, wherein the nucleic acid sample is obtained from a tissue or liquid biological sample of the subject.

3. The method of claim 1, wherein the nucleic acid sample is obtained from whole blood, PBMCs, plasma or serum.

4. The method of claim 1, wherein the nucleic acid sample is obtained from saliva or from buccal tissue.

5. The method of claim 1, wherein the nucleic acid sample is isolated in a form suitable for CRISPR/Cas9 enrichment.

6. The method of claim 1, wherein the nucleic acid sample from the subject which has been enriched for DNA sequences is enriched for the D4Z4 repeats on chromosome 4 by dephosphorylating the 5' ends of the nucleic acid, adding Cas9 ribonucleoprotein particles and gRNA specific for D4Z4, and cutting the dephosphorylated 5' ends using CRISPR/Cas9, and ligating sequencing adapters to the nucleic acid prior to the nanopore long-read sequencing.

7. The method of claim 1, wherein the nucleic acid sample has been enriched only for DNA comprising the D4Z4 repeat array.

8. The method of claim 1, wherein the CRISPR/Cas9 enrichment uses gRNAs comprising sequences from a P123811 region, 4qA (PLAM), or 4qB regions, which regions flank to D4Z4 repeat region and wherein an enriched array is a complete array containing P123811, D4Z4 and 4qA/4qB.

9. The method of claim 1, wherein the step of identifying a subject having FSHD1, comprises measuring the number of D4Z4 repeats in the D4Z4 repeat array and the methylation of bases in the permissive allele of the sequenced DNA.

10. The method of claim 1, further comprising identifying a subject having FSHD2 by performing nanopore long-read sequencing for DNA sequences containing the D4Z4 repeat array for SMCHD1, DNMT3B, or LRIf1 genes using CRISPR/Cas9 and guide RNAs (gRNA) which recognize DNA sequences flanking the D4Z4 repeat array and the SMCHD1, DNMT3B, or LRIF1 genes; detecting one or more mutations in SMCHD1, DNMT3B or LRIf1 genes, and/or measuring the methylation of bases in the permissive allele of the subject; and identifying the subject as having FSHD2 when the permissive allele of the subject are hypomethylated compared to those in normal control subject not having FSHD2 and when mutations in SMCHD1, DNMT3B, or LRIf1 regions are detected.

11. The method of claim 1, further comprising treating FSHD1, FSHD1 symptoms or providing genetic counseling to the subject identified as having FSHD1.

12. The method of claim 10, wherein the nucleic acid sample has been enriched for DNA comprising the SMCHD1 region.

13. The method of claim 10, wherein the nucleic acid sample has been enriched for DNA comprising the SMCHD1 region using gRNA selected from the group consisting of SEQ ID NOS: 5,6, 7, or 8.

14. The method of claim 10, wherein the nucleic acid sample has been enriched for DNA comprising the DNMT3B region.

15. The method of claim 10, wherein the nucleic acid sample has been enriched for DNA comprising the DNMT3B region using gRNAs selected from the group consisting of SEQ ID NOS: 9, 10, 11, or 12.

16. The method of claim 10, wherein the nucleic acid sample has been enriched for DNA comprising the LRIF 1 region.

17. The method of claim 10, wherein the nucleic acid sample has been enriched for DNA comprising the LRIF 1 region using gRNAs selected from the group consisting of SEQ ID NOS: 13, 14, 15, or 16.

18. The method of claim 10, further comprising detecting the presence or absence of a functional polyadenylation signal downstream of the last D4Z4 which stabilizes a DUX4 transcript when the 4qA allele is present.

19. The method of claim 1, wherein methylation is determined by base-calling of methylated bases identified by nanosequencing.

20. The method of claim 1, wherein methylation is determined by sodium bisulfite conversion, different enzymatic cleavage of DNA, or affinity capture of methylated DNA.

21. The method of claim 10, further comprising treating the subject identified as having FSHD2 for at least one FSHD symptom.

22. The method of claim 10, further comprising providing genetic counseling to the subject when FSHD is identified or informing the subject of a negative or differential diagnosis excluding FSHD when FSHD is not identified in the subject.

* * * * *